(12) United States Patent
Cornforth et al.

(10) Patent No.: US 9,555,058 B2
(45) Date of Patent: Jan. 31, 2017

(54) ANTIGEN PRESENTING CANCER VACCINE

(71) Applicant: CALIFORNIA STEM CELL, INC., Irvine, CA (US)

(72) Inventors: Andrew Cornforth, Irvine, CA (US); Robert Dillman, Irvine, CA (US)

(73) Assignee: Neostem Oncology, LLC, New York, NY (US)

( * ) Notice: Subject to any disclaimer, the term of this patent is extended or adjusted under 35 U.S.C. 154(b) by 0 days.

(21) Appl. No.: 14/352,983

(22) PCT Filed: Oct. 22, 2012

(86) PCT No.: PCT/US2012/061306
§ 371 (c)(1),
(2) Date: Apr. 18, 2014

(87) PCT Pub. No.: WO2013/059784
PCT Pub. Date: Apr. 25, 2013

(65) Prior Publication Data
US 2014/0314814 A1 Oct. 23, 2014

Related U.S. Application Data

(60) Provisional application No. 61/549,681, filed on Oct. 20, 2011, provisional application No. 61/594,304, filed on Feb. 2, 2012.

(51) Int. Cl.

| | | |
|---|---|---|
| *A61K 35/13* | (2015.01) | |
| *A61K 35/15* | (2015.01) | |
| *A61K 39/00* | (2006.01) | |
| *A61K 38/00* | (2006.01) | |
| *A61K 38/17* | (2006.01) | |
| *A61K 39/395* | (2006.01) | |

(52) U.S. Cl.
CPC .............. *A61K 35/13* (2013.01); *A61K 35/15* (2013.01); *A61K 38/17* (2013.01); *A61K 39/0011* (2013.01); *A61K 39/39558* (2013.01); *A61K 2039/5152* (2013.01); *A61K 2039/5154* (2013.01); *A61K 2039/545* (2013.01); *A61K 2039/55522* (2013.01); *A61K 2039/57* (2013.01)

(58) Field of Classification Search
CPC ......... A61K 35/13; A61K 35/15; A61K 38/00
USPC ............................................. 424/277.1, 184.1
See application file for complete search history.

(56) References Cited

U.S. PATENT DOCUMENTS

2006/0034811 A1\* 2/2006 Wallack et al. ............ 424/93.21
2009/0220530 A1 9/2009 Hu

FOREIGN PATENT DOCUMENTS

| JP | 2008517946 A | 5/2008 |
|---|---|---|
| JP | 2009502955 A | 1/2009 |
| JP | 2014530627 A | 11/2014 |
| JP | 2014533938 A | 12/2014 |
| WO | 99/42564 A2 | 8/1999 |
| WO | 01/29192 A2 | 4/2001 |
| WO | 2007/016340 A2 | 2/2007 |
| WO | 2008/126039 A2 | 10/2008 |
| WO | 2013059784 A1 | 4/2013 |

OTHER PUBLICATIONS

Lee et al. (Clinical Cancer Research, 2005, 11: 107-112).\*
Dolan et al. (J Immunol 2006, 176: 1447-1455).\*
Li, Y, et al. Efficient Cross-presentation Depends on Autophagy in Tumor Cells. Cancer Res. 2008; 68(17): 6889-6895.
Bateman, AR, et al. Viral Fusogenic Membrane Glycoproteins Kill Solid Tumor Cells by Nanapoptotic Mechanisms That Promote Cross Presentation of Tumor Antigens by Dendrite Cells. Cancer Res. 2002; 62(22): 6566-6578.
Li, B, et al. Autophagy facilitates major histocompatibility complex class I expression induced by IFN-gamma in B16 melanoma cells. Cancer Immunol Immunother. 2010; 59(2): 313-321.
Dillman R.O. et al., "Phase II trial of dendritic cells loaded with antigens from self-renewing, proliferating autologous tumor cells as patient-specific antitumor vaccines in patients with metastatic melanoma: final report" Cancer Biotherapy and Radiopharmaceuticals. 2009, vol. 24, pp. 311-319.
Li Y. et al., "Efficient cross-presentation depends on autophagy in tumor cells" Cancer Research. 2008, vol. 68(17), pp. 6889-6895.
Bateman A.R. et al., "Viral fusogenic membrane glycoproteins kill solid tumor cells by nonapoptotic mechanisms that promote cross presentation of tumor antigens by dendritic cells" Cancer Research. 2002, vol. 62(22), pp. 3566-6578.
Cornforth A.N. et al., "Aurtologous peripheral blood mononuclear cell recognition of autologous proliferating tumor cells in the context of a patient-specific vaccine trial" Journal of Biomedicine and Biotechnology. 2011, vol. 2011, pp. 1-6.
Cornforth A.N. et al., "Characterization of interferon-γ-treated melanoma tumor cells for use in dendritic cell-based immunotherapy" Cancer Biotherapy and Radiopharmaceuticals. 2011, vol. 26(3), pp. 345-351.
Alonso-Curbelo D. et al., "Self-killing of melanoma cells by cytosolic delivery of dsRNA: wiring innate immunity for a coordinated mobilization of endosomes, autophagosomes and the apoptotic machinery in tumor cells" Autophagy 2010, vol. 6(1), pp. 148-150.
Uhl M. et al., "Autophagy within the antigen donor cell facilitates efficient antigen cross-priming of virus-specific CC8+ T cells" Cell Death Differ. 2009, vol. 16(7), pp. 991-1005.

(Continued)

*Primary Examiner* — Yan Xiao
(74) *Attorney, Agent, or Firm* — Chiesa Shahinian & Giantomasi PC

(57) ABSTRACT

The disclosure provides reagents, methods, and kits, for treating melanoma. The reagent encompasses interferon-gamma (IFN-gamma) responsive melanoma cells, where the cells are autophagic and non-apoptotic melanoma cells, and where the cells express MHC Class II. In another aspect, the reagent encompassed dendritic cells loaded with the IFN-gamma responsive, non-apoptotic, MHC Class II-expressing melanoma cells.

4 Claims, 24 Drawing Sheets

(56) References Cited

OTHER PUBLICATIONS

Strioga, M.M., et al., "Therapeutic dendritic cell-based cancer vaccines: The state of the art", Critical Reviews in Immunology, 2013, vol. 33, pp. 489-547.
Romero, P.R., et al., "Ex vivo staining of metastatic lymph nodes by class 1 major histocompatibility complex retramers reveals high numbers of antigen-experienced tumor-specific cytolitic T lymphocytes", J. Exp. Med, 1998, vol. 188, pp. 1641-1650.

* cited by examiner

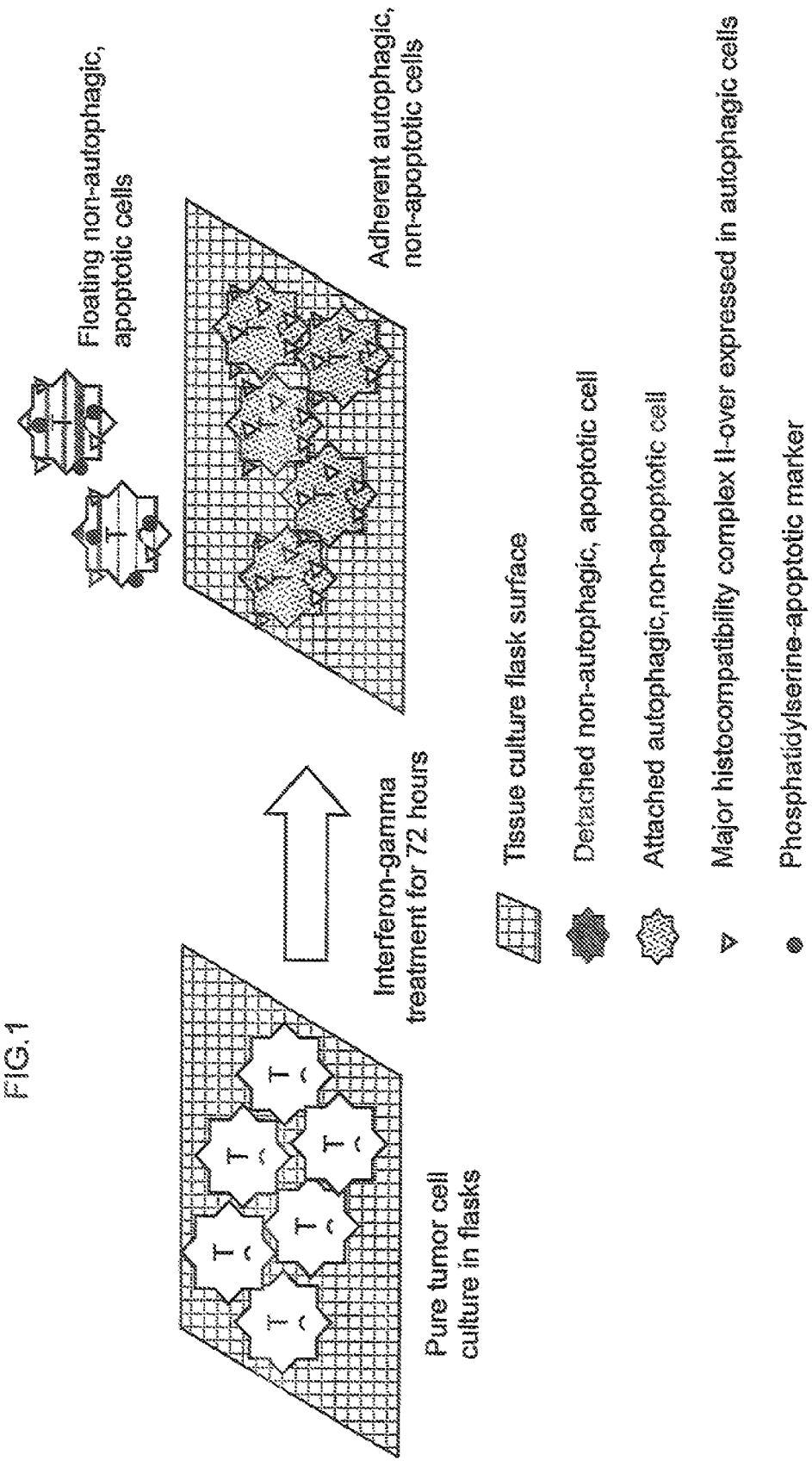

ANTIGEN PRESENTING CANCER VACCINE

RELATED APPLICATIONS

The present application is a national phase application of PCT/US2012/061306 filed on Oct. 22, 2013 which claims the full Paris Convention priority to and benefit of U.S. Provisional Application No. 61/549,681, filed on Oct. 20, 2011, and U.S. Provisional Application No. 61/594,304, filed on Feb. 2, 2012, all of which are incorporated by this reference, as if fully set forth in their entirety herein.

FIELD

The present disclosure relates to treating melanoma, screening subjects suitable for treatment, compositions of matter, methods and kits.

BACKGROUND

Cancer is distinguished by the lack of effective immune response against the cancer. Lack of immune response can result, for example, from the fact that many tumor antigens are "self-antigens," from lack of expression of MHC by the tumor cells and consequent lack of presentation of tumor antigens by the tumor cells, from the association of macrophages with tumors where the macrophages express cytokines that reduce immune response, and from the immunosuppressive activity of T regulatory cells (Tregs). Lack of immune response against tumors also results from the fact that tumor cells tend not to express molecules that stimulate innate immune response, that is, molecules that stimulate toll-like receptors (TLRs) or nucleotide-binding oligomerization domain (NOD)-like receptors). Cancer encompasses solid tumors as well as the hematological cancers, such as the leukemias and the myelodysplastic syndromes.

The immune system encompasses cellular immunity, humoral immunity, and complement response. Cellular immunity includes a network of cells and events involving dendritic cells, CD8$^+$ T cells (cytotoxic T cells; cytotoxic lymphocytes), and CD4$^+$ T cells (helper T cells). Dendritic cells (DCs) acquire polypeptide antigens, where these antigens can be acquired from outside of the DC, or biosynthesized inside of the DC by an infecting organism. The DC processes the polypeptide, resulting in peptides of about ten amino acids in length, transfers the peptides to either MHC class I or MHC class II to form a complex, and shuttles the complex to the surface of the DC. When a DC bearing a MHC class I/peptide complex contacts a CD8$^+$ T cell, the result is activation and proliferation of the CD8$^+$ T cell. Regarding the role of MHC class II, when a DC bearing a MHC class II/peptide complex contacts a CD4$^+$ T cell, the outcome is activation and proliferation of the CD4$^+$ T cell (Munz, et al. (2010) Curr. Opin. Immunol. 22:89-93; Monaco (1995) J. Leukocyte Biol. 57:543-547; Robinson, et al (2002) Immunology 105:252-262). Although dendritic cells presenting antigen to a T cell can "activate" that T cell, the activated T cell might not be capable of mounting an effective immune response. Effective immune response by the CD8$^+$ T cell often requires prior stimulation of the DC by one or more of a number of interactions. These interactions include direct contact of a CD4$^+$ T cell to the DC (by way of contact the CD4$^+$ T cell's CD40 ligand to the DC's CD40 receptor), or direct contact of a TLR agonist to one of the dendritic cell's toll-like receptors (TLRs).

Humoral immunity refers to B cells and antibodies. B cells become transformed to plasma cells, and the plasma cells express and secrete antibodies. Naïve B cells are distinguished in that they do not express the marker CD27, while antigen-specific B cells do express CD27 (Perez-Andres, et al. (2010) Cytometry Part B 78B (Suppl. 1) S47-S60). The secreted antibodies can subsequently bind to tumor antigens residing on the surface of tumor cells. The result is that the infected cells or tumor cells become tagged with the antibody. With binding of the antibody to the infected cell or tumor cell, the bound antibody mediates killing of the infected cell or tumor cell, where killing is by NK cells. Although NK cells are not configured to recognize specific target antigens, in the way that T cells are configured to recognize target antigens, the ability of NK cells to bind to the constant region of antibodies, enables NK cells to specifically kill the cells that are tagged with antibodies. The NK cell's recognition of the antibodies is mediated by Fc receptor (of the NK cell) binding to the Fc portion of the antibody. This type of killing is called, antibody-dependent cell cytotoxicity (ADCC). NK cells can also kill cells independent of the mechanism of ADCC, where this killing requires expression of MHC class I to be lost or deficient in the target cell (see, e.g., Caligiuri (2008) Blood 112:461-469).

The technique of "delayed type hypersensitivity response" can be used to distinguish between immune responses that mainly involve cellular immunity or mainly involve humoral immunity. A positive signal from the delayed type hypersensitivity response indicates a cellular response (see, e.g., Roychowdhury, et al. (2005) AAPS J. E834-E846).

Autophagy is a homeostatic process by which cytosolic components and organelles are delivered to the lysosome for degradation. Autophagy is also associated with innate and adaptive immune responses to intracellular pathogens whereby cytosolic antigens are loaded onto major histocompatibility complex (MHC) class II molecules for CD4$^+$ T-cell recognition.

DESCRIPTION

As used herein, including the appended claims, the singular forms of words such as "a," "an," and "the" include their corresponding plural references unless the context clearly dictates otherwise. All references cited herein are incorporated by reference to the same extent as if each individual publication, patent, published patent application, and sequence listing, as well as figures and drawings in said publications and patent documents, was specifically and individually indicated to be incorporated by reference.

SUMMARY OF THE DISCLOSURE

Disclosed is a population of mammalian dendritic cells comprising melanoma-specific peptides from a given subject that has melanoma and comprises melanoma cells; wherein said melanoma-specific peptides are acquired in vitro by dendritic cells from said melanoma cells that are not treated in vitro with IFN-gamma or IFN-gamma mimetic, wherein greater than 60 percent (%) of said melanoma cells that are not treated in vitro with IFN-gamma or IFN-gamma mimetic are autophagic and non-apoptotic, and wherein the dendritic cells and melanoma cells are from the same subject.

Also disclosed is the above population of mammalian dendritic cells, wherein: greater than 80% of said melanoma cells are autophagic and non-apoptotic.

What is disclosed are the above dendritic cells, wherein essentially all of the melanoma cells that are not treated with IFN-gamma or IFN-gamma mimetic are incapable of cell division; as well as the above dendritic cells wherein essentially all of the melanoma cells that are not treated with IFN-gamma or IFN-gamma mimetic are irradiated and incapable of cell division; as well as the above dendritic cells, wherein at least 80% of the melanoma cells that are not treated with IFN-gamma or IFN-gamma mimetic are irradiated and incapable of cell division; as well as the above dendritic cells wherein at least 80% of the melanoma cells that are not treated with IFN-gamma or IFN-gamma mimetic are treated with a nucleic acid cross-linker and are incapable of cell division.

Also disclosed is a vaccine comprising the above population of the above mammalian dendritic cells.

Also disclosed, are the above dendritic cells, wherein essentially all of the melanoma-specific peptides are from melanoma cells that are incapable of cell division Furthermore, what is disclosed are the above dendritic cells, wherein essentially all of the melanoma-specific peptides are from melanoma cells that are incapable of cell division because the melanoma cells are irradiated.

Disclosed are the above dendritic cells, wherein essentially all of the melanoma-specific peptides are from melanoma cells that are incapable of cell division because the chromosomes of the melanoma cells are cross-linked by a nucleic acid cross-linking agent.

Also disclosed are the above dendritic cells, comprising melanoma-specific peptides that are from melanoma cells that are treated with radiation.

Disclosed are the above dendritic cells, comprising melanoma-specific peptides, wherein all of said peptides are from melanoma cells that are treated with radiation.

Also disclosed are the above dendritic cells, that comprise one or more peptides derived from a melanoma-specific antigen that S-100, HMB-45, Mel-2, Melan-A, Mel-5, MAGE-1, MART-1, or Tyrosinase.

What is disclosed, are the above dendritic cells, wherein essentially all of the melanoma-specific peptides are from melanoma cells that are treated in vitro to be incapable of cell division.

Also disclosed, are the above dendritic cells, wherein the given subject is a human subject.

Disclosed are the above dendritic cells, wherein the given subject is a mammal that is not human.

Disclosed is a melanoma vaccine comprising at least one mature dendritic cell from a subject that has melanoma, wherein the at least one mature dendritic cell had been contacted with at least one melanoma tumor cell from the same subject, wherein the at least melanoma tumor cell that is contacted with the at least one mature dendritic cell is non-dividing, autophagic, and non-apoptotic.

Also disclosed is a method for stimulating immune response against a melanoma-specific antigen comprising administering an immune-stimulatory amount of the dendritic cells of claim 1 to a subject.

What is disclosed is wherein the subject has melanoma and does comprise melanoma cells.

What is disclosed is the above method, wherein the immune response that is stimulated comprises one or more of CD4+ T cell response, CD8+ T cell response, and B cell response.

What is disclosed is the above method, wherein the CD4+ T cell response, CD8+ T cell response, or B cell response, can be measured by ELISPOT assays, by intracellular cytokine staining assays, by tetramer assays, or by detecting antigen-specific antibody production.

Also disclosed is the above method, wherein the immune response comprises a survival time that comprises 2-year overall survival (OS), and where the 2-year overall survival is at least 60%.

What is disclosed is the above method, wherein the administration comprises subcutaneous injections of the vaccine.

What is disclosed is the above method, wherein the administration comprises injections of the vaccine given weekly for three months and then monthly for five months.

Also disclosed is the above method for preparing a dendritic cell vaccine, involving melanoma cells and dendritic cells from the same subject, the method comprising: one or more melanoma cells is treated with an agent that prevents cell division; the one or more melanoma cells are not treated in vitro with interferon-gamma (IFN-gamma) or with an IFN-gamma mimetic; melanoma cells that are autophagic and non-apoptotic are selected; melanoma cells that are non-autophagic and apoptotic are rejected; and, wherein the melanoma cells that are autophagic and non-apoptotic are provided to one or more autologous dendritic cells, or, wherein peptides derived from the melanoma cells that are autophagic and non-apoptotic are provided to one or more autologous dendritic cells.

What is disclosed is a composition comprising: at least one melanoma cell that is not treated with interferon-gamma (IFN-gamma) from a first subject, and at least one antigen presenting cell (APC) from the same first subject, wherein the melanoma cell is: autophagic; and non-apoptotic.

Also, what is disclosed is the above composition, wherein the melanoma cell is MHC class II-expressing.

Also disclosed is the above composition, wherein the APC is a dendritic cell, a macrophage, or a B cell.

Disclosed is the above composition, wherein the at least one melanoma cell comprises melanoma-specific peptides, and wherein the melanoma specific-peptides are substantially not contained in said APCs and are substantially not processed by said APCs.

Also disclosed is the above composition, where the melanoma cells comprise melanoma-specific peptides, and wherein the melanoma specific-peptides are substantially contained in said APCs and are partially or substantially processed in said APCs. Also disclosed is the above composition, wherein the melanoma cell is loaded into the APC. What is disclosed is the above composition wherein the melanoma cells is not loaded into the APC.

Disclosed is the above composition, wherein autophagy is demonstrated by a test that assays microtubule-associated protein light chain 3 (LC3).

Disclosed is the above composition, wherein the cells are demonstrated to be non-apoptotic using at least one of the reagent, 7-aminoactinomycin D (7-ADD), or the reagent, annexin.

What is disclosed is a method of stimulating immune response in a subject having melanoma and comprising melanoma cells, wherein the subject is the same subject as the first subject, comprising administering an immunology effective amount of the above composition.

What is disclosed is the above composition, wherein at least 90% of the melanoma cells are not treated in vitro with IFN-gamma, and less than 10% of the melanoma cells are treated in vitro with IFN-gamma.

What is disclosed is a method for manufacturing the above vaccine or the above composition, comprising contacting at least one melanoma tumor cell to at least one antigen presenting cell (APC), wherein the at least one melanoma tumor cell is from a first human subject, and wherein the at least one APC is from the same first human subject.

What is disclosed is a method for preparing a dendritic cell vaccine, comprising: treating melanoma cells acquired from a first subject with an agent that prevents cell division; wherein the melanoma cells are not treated in vitro with IFN-gamma or an IFN-gamma mimetic; selecting melanoma cells that are autophagic and non-apoptotic; and, contacting the selected melanoma cells with autologous dendritic cells from the same first subject.

What is disclosed is a composition that comprises a dendritic cell vaccine, as prepared by the above method.

Disclosed is a method for stimulating immune response against a melanoma-specific antigen, comprising administering the above composition to a subject that has melanoma.

Disclosed is a composition comprising at least one melanoma cell from a first subject, and at least one antigen presenting cell (APCs) from the same first subject, wherein the melanoma cell is: autophagic; non-apoptotic; and MHC class II-expressing. In the present disclosure an IFN-gamma-treated melanoma cell is not loaded into the APC, and wherein an IFN-gamma treated melanoma cell is not loaded into the APC. In another aspect, what is embraced is the above composition wherein the melanoma cell is from a subject with Stage I, Stage II, Stage III, or Stage IV melanoma. Additionally, what is contemplated is the above composition, related kits, and related methods, wherein the APC comprises at least one dendritic cell.

In one aspect, the pharmaceutical composition, reagent, and related methods, of the present disclosure uses a preparation of cancer cells that, is 7-AAD negative and annexin V negative. This population can be, e.g., about 99% 7-AAD negative and about 99% annexin V negative, or at least 95% 7-AAD negative and at least 95% annexin V negative, or at least 90% 7-AAD negative and at least 90% annexin V negative, to provide non-limiting examples.

Furthermore, what is embraced is the above composition, wherein autophagy is demonstrated by a test that assays microtubule-associated protein light chain 3 (LC3); and the above composition, wherein the cells are demonstrated to be non-apoptotic using at least one of the reagent, 7-aminoactinomycin D (7-AAD), or the reagent, annexin.

In methods aspects, what is provided a method of manufacturing the above-disclosed composition, comprising removing at least one melanoma cell from the first subject, removing at least one APC from the first subject, and allowing the melanoma cell to contact the APC; as well as a method for stimulating immune response against a melanoma in a subject or patient, comprising administering the above composition of to a subject.

In a kit aspect, the present disclosure provides a kit for testing immune response against a tumor antigen in a subject, wherein the subject is treated by one or more of the above methods, and wherein the kit comprises a reagent that detects humoral immune response, cellular immune response, or innate immune response.

DEFINITIONS

Immune-stimulatory amount, without limitation, can be an amount that increases ELISPOT assay results by a measurable amount, that increases ICS assay results by a measurable amount, that increases tetramer assay results by a measurable amount, that increases the blood population of antigen-specific $CD4^+$ T cells by a measurable amount, that increases the blood population of antigen-specific $CD8^+$ T cells by a measurable amount, or where the increase is by at least 10%, 20%, 30%, 40%, 50%, 60%, 70%, 80%, 90%, 100%, 1.5-fold, 2.0-fold, 3.0-fold, and the like, when compared to a suitable control. A suitable control can be a control vaccine, where dendritic cells are not loaded with melanoma cells, or are not loaded with peptide derived from melanoma cells.

The term "melanoma-specific antigen" encompasses antigens that are frequently associated with melanoma, and where the antigen is considered to be unique to melanoma, as opposed to being associated with other cancers, and in addition, the term "melanoma-specific antigens" encompasses antigens that are frequently associated with melanoma, and where the antigen is also associated with other types of cancer, such as breast cancer, colorectal cancer, and the like.

"Irradiated," in the context of irradiating melanoma cells for the present disclosure, is preferably by gamma-irradiation, but also encompasses irradiation by x-rays, electrons, neutrons, protons, electromagnetic irradiation, visible light, ultraviolet light, and so on. In one aspect, the irradiation functions to prevent cell division of the melanoma cells. In another aspect, the irradiation prevents cell division, but also denatures cellular proteins. As an alternative to irradiation, the present disclosure prevents cell division of melanoma cells by way of physical disruption, e.g., sonication, cavitation, dehydration, ion depletion, or by toxicity from exposure to one or more salts.

The term "percent," as in "greater than 60% of the melanoma-specific peptides," refers to the number of peptide molecules, and not to the number of different antigenically distinct peptides. The term "percent," as in "greater than 80% of the melanoma-specific peptides," refers to the number of peptide molecules, and not to the number of different antigenically distinct peptides. The term "percent," as in "less than 40% of the melanoma-specific peptides," refers to the number of peptide molecules, and not to the number of antigenically distinct peptides. The term "percent," as in "less than 20% of the melanoma-specific peptides," refers to the number of peptide molecules, and not to the number of antigenically distinct peptides, and the like.

The term "peptides," as in "greater than 60% of the melanoma-specific peptides," refers to the sum of the number of peptide molecules, oligopeptides molecules, and polypeptide molecules. The term "peptides," as in "greater than 80% of the melanoma-specific peptides," refers to the sum of the number of peptide molecules, oligopeptides molecules, and polypeptide molecules. The term, "peptides," as in "less than 40% of the melanoma-specific peptides," refers to the sum of the number of peptide molecules, oligopeptides molecules, and polypeptide molecules. The term, "peptides," as in "less than 20% of the melanoma-specific peptides," refers to the sum of the number of peptide molecules, oligopeptides molecules, and polypeptide molecules, and the like.

"Derived from," in the context of peptides derived from one or more cancer cells, encompasses the following. The cancer cell can be broken, for example, by a homogenizer or by osmotic bursting, resulting in a crude extract. Peptides, oligopeptides, and polypeptides of the crude extract can be exposed to dendritic cells, followed by processing of the peptides by the dendritic cells. Derived from also encompasses providing dendritic cells with intact cancer cells, where the cancer cells are living, or where the cancer cells have been treated with irradiation but are still metabolically active, or where the cancer cells have been treated with a nucleic acid cross-linking agent but are still metabolically active. "Derived from" includes mixtures of cancer cell debris, free cancer cell proteins, and irradiated cancer cells, that are taken up by dendritic cells, and therefore are derived from the cancer cells.

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor. An antagonist, as it relates to a ligand and receptor, comprises a molecule, combination of molecules, or a complex, that inhibits, counteracts, down-regulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

Unless expressly stated otherwise, or dictated otherwise by the context, the term "expression" encompasses the following. Expression encompasses the biosynthesis of mRNA, polypeptide biosynthesis, polypeptide activation, e.g., by post-translational modification, or an activation of expression by changing the subcellular location or by recruitment to chromatin. In other words, "increased expression" encompasses increased biosynthesis, or increased activity that is caused by phosphorylation, or an increased activity that is caused by migration from the cytosol to the nucleus.

Antigen presenting cells (APCs) are cells of the immune system used for presenting antigen to T cells. APCs include dendritic cells, monocytes, macrophages, marginal zone Kupffer cells, microglia, Langerhans cells, T cells, and B cells (see, e.g., Rodriguez-Pinto and Moreno (2005) Eur. J. Immunol. 35:1097-1105). Dendritic cells occur in at least two lineages. The first lineage encompasses pre-DC1, myeloid DC1, and mature DC1. The second lineage encompasses $CD34^{++}CD45RA$-early progenitor multipotent cells, $CD34^{++}CD45RA^{+}$ cells, $CD34^{++}CD45RA^{++}$ $CD4^{+}$ $IL-3Ralpha^{++}$ pro-DC2 cells, $CD4^{+}CD11c^{-}$ plasmacytoid pre-DC2 cells, lymphoid human DC2 plasmacytoid-derived DC2s, and mature DC2s (see, e.g., Gilliet and Liu (2002) J. Exp. Med. 195:695-704; Bauer, et al. (2001) J. Immunol. 166:5000-5007; Arpinati, et al. (2000) Blood 95:2484-2490; Kadowaki, et al. (2001) J. Exp. Med. 194:863-869; Liu (2002) Human Immunology 63:1067-1071; McKenna, et al. (2005) J. Virol. 79:17-27; O'Neill, et al. (2004) Blood 104:2235-2246; Rossi and Young (2005) J. Immunol. 175: 1373-1381; Banchereau and Palucka (2005) Nat. Rev. Immunol. 5:296-306).

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition. The severity of a disease or disorder, as well as the ability of a treatment to prevent, treat, or mitigate, the disease or disorder can be measured, without implying any limitation, by a biomarker or by a clinical parameter. Biomarkers include blood counts, metabolite levels in serum, urine, or cerebrospinal fluid, tumor cell counts, cancer stem cell counts, tumor levels. Tumor levels can be determined by the RECIST criteria (Eisenhauer, et al. (2009) Eur. J. Cancer. 45:228-247). Expression markers encompass genetic expression of mRNA or gene amplification, expression of an antigen, and expression of a polypeptide. Clinical parameters include progression-free survival (PFS), 6-month PFS, disease-free survival (DFS), time to progression (TTP), time to distant metastasis (TDM), and overall survival, without implying any limitation.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, epitope tags fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

Methods for Assessing Immune Response

The present disclosure also provides ELISPOT assays, intracellular cytokine staining (ICS), and tetramer assays, for characterizing immune response (see, e.g., of US 2007/0190029 of Pardoll; Chattopadhyay (2008) Cytometry A. 2008 73:1001-1009; Vollers (2008) Immunology. 123:305-313; Lalvani, et al. (1997) J. Exp. Med. 186:859-865; Waldrop (1997) J. Clin. Invest. 99:1739-1750; Hudgens (2004) J. Immunol. Methods 288:19-34; Goulder (2001) J. Virol. 75:1339-1347; Goulder (2000) J. Exp. Med. 192: 1819-1831; Anthony (2003) Methods 29:260-269; Badovinac and Harty (2000) J. Immunol. Methods 238:107-117). Immune response in a patient can be assessed by endpoints that are used in oncology clinical trials, including objective response (RECIST criteria), overall survival, progression-free survival (PFS), disease-free survival, time to distant metastasis, 6-month PFS, 12-month PFS, and so on.

Vaccines

Dendritic cell vaccine of the present disclosure can be administered by intradermal, intranodal, mucosal, or subcutaneous routes, or any combination of the above. Each dose can comprise about $10 \times 10^3$ dendritic cells, $20 \times 10^3$ cells, $50 \times 10^3$ cells, $100 \times 10^3$ cells, $200 \times 10^3$ cells, $500 \times 10^3$ cells, $1 \times 10^6$ cells, $2 \times 10^6$ cells, $20 \times 10^6$ cells, $50 \times 10^6$ cells, $100 \times 10^6$ cells, $200 \times 10^6$, $500 \times 10^6$, $1 \times 10^9$ cells, $2 \times 10^9$ cells, $5 \times 10^9$ cells, $10 \times 10^9$ cells, and the like. Administration frequency can be, e.g., once per week, twice per week, once every two weeks, once every three weeks, once every four weeks, once per month, once every two months, once every three months, once every four months, once every five months, once every six months, and so on. The total number of days where administration occurs can be one day, on 2 days, or on 3, 4, 5, 6, 7, 8, 9, 10, 11, 12, 13, 14, 15, 16, 17, 18, 19, or 20 days, and so on. It is understood that any given administration might involve two or more injections on the same day. In one aspect, the disclosure involves loading dendritic cells with whole tumor cells, where at least 10%, where at least 20%, at least 30%, at least 40%, at least 50%, at least 60%, at least 70%, at least 80%, at least 90%, at least 95%, or at least 99%, of the melanoma cell-derived protein that is loaded into the dendritic cells resides in whole tumor cells. In non-limiting embodiments, dendritic cell vaccine is held in a flask, in a vial, in a bottle, in a syringe, in a catheter, in a cannula, and so on. For administration, at least 20%, at least 30%, at least 40%, at least 50%, at least 60%, at least 70%, at least 80%, at least 90%, at least 95%, at least 99%, of the dendritic cells that are administered are mature dendritic cells.

Vaccine Homogeneity

In embodiments, the disclosure provides a vaccine comprising dendritic cells that contain melanoma peptides derived from in vitro loading, where the vaccine comprises dendritic cells (sum of DCs containing melanoma peptide, and DCs not containing melanoma peptides) at a ratio of dendritic cells/melanoma cells of at least 5/95, 10/90, 20/80, 30/70, 40/60, 50/50, 60/40, 70/30, 80/20, 90/10, 95/5, 98/2, 99/1, and the like. Also provided, is a vaccine comprising dendritic cells that contain melanoma peptides derived from in vitro loading, where the vaccine comprises dendritic cells (sum of DCs containing melanoma peptide, and DCs not containing melanoma peptides) at a ratio of [dendritic cells]/[cells that are neither DCs nor melanoma], of at least 5/95, 10/90, 20/80, 30/70, 40/60, 50/50, 60/40, 70/30, 80/20, 90/10, 95/5, 98/2, 99/1, and the like. The disclosure provides a compartmented container, where a first compartment contains melanoma cells, and a second compartment contains dendritic cells. The two compartments can be separated by a membrane, filter, valve, conduit, coupler, which prevents the melanoma cells from contacting the dendritic cells, but where manual transfer, or where removal of the membrane or opening of the valve allows the melanoma cells to contact the dendritic cells, allowing loading of melanoma cells, melanoma cell fragments, and/or melanoma peptides, on the dendritic cells.

Interferon-Gamma Mimetics

The present disclosure encompasses mimetics, for example, interferon-gamma mimetics, such as mimetic peptide 95-132 (Ahmed (2007) J. Immunol. 178:4576-4583; Fulcher (2008) FEBS Lett. 582:1569-1574). IFN-mimetic encompasses, e.g., an antibody that has the same agonist activity of interferon-gamma.

Inactivating Melanoma Cells

The present disclosure provides compositions and methods, where cancer cells are inactivated, for example, by radiation or by way of nucleic acid cross-linkers. Exemplary cross-linkers, have the ability to cross-link DNA but to leave proteins unmodified. A nucleic acid alkylator can be beta-alanine, N-(acridin-9-yl), 2-[bis(2-chloroethyl)amino]ethyl ester. In some embodiments, the nucleic acid targeted compound is a psoralen compound activated by UVA irradiation. For instance, the nucleic acid targeting compound can be 4'-(4-amino-2-oxa)butyl-4,5',8-trimethylpsoralen (also referred to herein as "S-59"). Cells can be inactivated with 150 micromolar of psoralen S-59 and 3 J/cm$^2$ UVA light (FX 1019 irradiation device, Baxter Fenwal, Round Lake, Ill.). The inactivation with S-59 is referred to as photochemical treatment and results in complete inactivation of the cells. Various concentrations of nucleic acid cross-linked agent can be tested for efficacy in inactivating cells, for example, for efficacy in preventing cell division. S-59 is distinguished by its ability to cross-link nucleic acids, but to leave proteins intact an unmodified. Cells can be suspended in 5 mL of saline containing 0, 1, 10, 100, and 1000 nM of psoralen S-59. Each sample can be irradiated as follows. The S-59 can be added at a concentration of 100 nM. Samples can be UVA irradiated at a dose of approximately 2 J/cm$^2$ (FX1019 irradiation device, Baxter Fenwal, Round Lake, Ill.). Each sample can then transferred to a 15 mL tube, centrifuged, and the supernatant removed, and then washed with 5 mL saline, centrifuged and the supernatant removed and the final pellet suspended in 0.5 mL of saline (U.S. Pat. No. 7,833,775 of Dubensky and U.S. Pat. No. 7,691,393 of Dubensky).

Enriching for Melanoma Cells that are Non-Apoptotic

A population of melanoma cells can be enriched in melanoma cells that are non-apoptotic, for example, by use of the technique that separates non-apoptotic and autophagic cells from cells that are non-autophagic and apoptotic, where separation is by the adhesion of the autophagic and non-apoptotic cells to a surface, where the other cells are floating. A population enriched in non-apoptotic melanoma cells can also be acquired by removing apoptotic cells by way of an antibody specific for phosphatidyl serine. Techniques for removing cells by way of immobilized antibodies are available (Onodera (1998) Ther. Apher. 2:37-42). Antibodies specific for phosphatidylserine are available (e.g., EMD Millipore, Billerca, Mass.). Also, bulk population of melanoma cells can be labeled with fluorescent anti-phosphatidylserine antibodies, where the tagged apoptotic melanoma cells are removed by flow cytometry, affinity chromatography, immunomagnetic separation (see, e.g., Hoeppener (2012) Recent Results Cancer Res. 195:43-58; Dainiak (2007) Adv. Biochem. Eng. Biotechnol. 106:1-18).

Inhibitors of Apoptosis

Z-VAD (Z-VAD-fmk), an inhibitor of apoptosis, can be acquired from, e.g., Enzo Life Sciences (Exeter, UK), R & D Systems (Minneapolis, Minn.), Tocris Biosciences (Bristol, UK), BioMol (Plymouth Meeting, Pa.), and EMD Chemicals (Gibbstown, N.J.). Z-VAD-fmk is a synthetic peptide, Z-Val-Ala-Asp(OMe)-CH$_2$F. Caspases are cysteine-aspartic acid-specific members of the protease family. Caspases are activated by a death receptor ligation, e.g., TRAIL, FAS, by DNA damage, stress, serum starvation and in some cell types, interferons. Caspases play a critical role in the highly regulated process of apoptosis that includes nuclear fragmentation, chromatin condensation, and loss of cytoplasmic integrity. The pan-capase inhibitor, z-VAD-fmk (carbobenzoxy-valyl-alanyl-aspartyl-[O-methyl]-fluoromethylketone) irreversibly binds the catalytic site of caspase proteases and inhibits their function in inducing apoptosis. Inhibiting the ability of cells to undergo apoptosis in response to IFN-gamma can be a means by which cells that are non-apoptotic but autophagic and be generated without the steps of selection by the washing to remove floating apoptotic cells.

The disclosure provides pharmaceuticals, reagents, kits including diagnostic kits, that wherein the pharmaceuticals, reagents, and kits, comprise dendritic cells, antibodies, or antigens. What is also provided are methods for administering compositions that comprise at least one dendritic cell and at least one antigen, methods for stimulating antibody formation, methods for stimulating ADCC, methods for stimulating complement-dependent cytotoxicity, and methods and kits for determining patient suitability, for determining patient inclusion/exclusion criteria in the context of a clinical trial or ordinary medical treatment, and for predicting response to the pharmaceutical or reagent. Complement-dependent cytotoxicity is described (see, e.g., Goodman, et al. (1990) J. Clin. Oncol. 8:1083-1092; Cheson (2010) J. Clin. Oncol. 28:3525-3530). The pharmaceutical compositions, reagents, and related methods, of the disclosure encompass CD83 positive dendritic cells, where CD83 is induced by loading with IFN-gamma-treated cancer cells. In a CD83 aspect of the disclosure, the CD83 is induced by at least 2%, at least 3%, at least 4%, 6%, 7%, 8%, 9%, 10%, and the like.

FIGURES

FIG. 1 reveals a graphic of cultured tumor cells before treatment with IFN-gamma (left) and after treating with IFN-gamma for 72 hours (right). After treatment, the cultured tumor cells are either floating, non-autophagic, and apoptotic, or adherent, autophagic, and non-apoptotic. The floating cells are shown expressing the apoptotic marker, phosphatidyl serine. The floating cells are shown with relatively few expressed MHC class II, while the adherent cells are shown with over-expressed MHC class II.

FIGS. 2A-D show characterization of IFN-gamma treated autologous tumor cells used for loading dendritic cells. Autologous melanoma tumor cells were treated with or without 1000 IU/mL IFN-gamma for 72 hours in 15% FBS/ECS in RPMI, harvested and irradiated with 100Gy and cryopreserved. Cells were then thawed in AIMV and a sample taken for flow cytometry and for preparation of cell lysates for immunoblotting prior to antigen loading of DCs. An example of four separate autologous melanoma cell lines is shown (FIG. 2A, FIG. 2B and FIG. 2C). Induction major histocompatibility complexes by IFN-gamma treatment of autologous tumor cells (FIG. 2D). Tumor cells were harvested after being treated with or without 1000 IU/mL IFN-gamma for 72 hours and then assayed for MHC class I and class II. Control isotype antibodies were used to identify positive populations. Dark data points indicate median mean fluorescent plus/minus 95% confidence interval. N=65. After irradiation, melanoma cells are checked by assays to ensure that there is not any mitosis.

In one aspect, the disclosure excludes non-autologous tumor cells for loading dendritic cells, and excludes methods of using non-autologous tumor cells for loading dendritic cells.

FIGS. 3A and 3B describe phenotype of dendritic cells loaded with autologous melanoma cell lines treated with or without interferon-gamma. A set of four autologous melanoma cell lines were treated with or without 1000 IU/mL of IFN-gamma for 72 hours, irradiated and cryopreserved. The cells were then thawed in AIMV and combined with autologous dendritic cells for approximately 24 hours prior to harvest and assaying by flow cytometry for the expression of CD80, CD83, CD86 and MHC class II (FIG. 3A). The data is summarized in FIG. 3B. Averages±SD are shown, n=4.

FIGS. 4A and 4B show phenotype of dendritic cells used for dose preparation. Samples of DC prior to loading (Pre-ATC Load DC, N=53) and after loading (Post-ATC Load DC, N=65) with IFN-gamma treated, irradiated autologous tumor cells were accessed by flow cytometry for the expression of CD80, CD83, CD86 and MHC class II. FACS Caliber® beads were used to set the initial flow cytometer instrument settings which were then held constant throughout the collection of data (FIG. 4A). Values of percent expression and mean fluorescence intensity (MFI)±SD are compared in FIG. 4B for Pre-ATC and Post-ATC loading. *p=0.019 and **p=0.0009.

FIGS. 5A to 5C show interferon-gamma treated melanoma cells undergo autophagy. A selection of commercially available melanoma cell lines were incubated with 1000 IU/mL IFN-gamma for 72 hours in 5% FBS/RMPI. Phase-contrast photomicrographs of SK-5-Mel cell cultures were taken at the end of the incubation period (FIG. 5A) showing enlarged cells with vacuoles reminiscent of autophagosomes. Confirmation of the formation of autophagosomes was demonstrated by transfection with GFP-LC3B constructs prior to treatment with IFN-gamma (FIG. 5B). Autophagy induction after IFN-gamma treated was confirmed by western blotting using an antibody for LC3B (FIG. 5C) which identifies a faster migrating form of LC3 that has been shown to be associated with autophagic vessel formation.

FIGS. 6A and 6B reveal apoptosis and autophagy induced in response to interferon-gamma. SK-5-Mel cells were incubated with 1000 IU/mL of IFN-gamma for 72 hours after which non-adherent and adherent populations were collected and assayed for apoptosis and autophagy by flow cytometry using 7-MD and Annexin-V (FIG. 6A). Enzo Cyto-ID Autophagy Detection Dye was used to measure autophagy by flow cytometry by measuring the mean intensity peak shift of dye provided by the manufacturer (FIG. 6B). Fold changes in the peak shift in comparison to 5% FBS/RPMI are shown in FIG. 6C with serum-free as positive control for the induction of autophagy.

FIG. 7 discloses autophagy induction after blocking of caspase activity did not affect the induction of autophagy in response to IFN-gamma in melanoma cells. SK-5-Mel cells were treated with 1000 IU/mL of IFN-gamma in the presence of 20 uM of the pan-caspase inhibitor z-VAD or its control compound, z-FA for 72 hours. The cells were harvested and assayed for autophagy by flow cytometry as in FIG. 6C.

Figure 13:
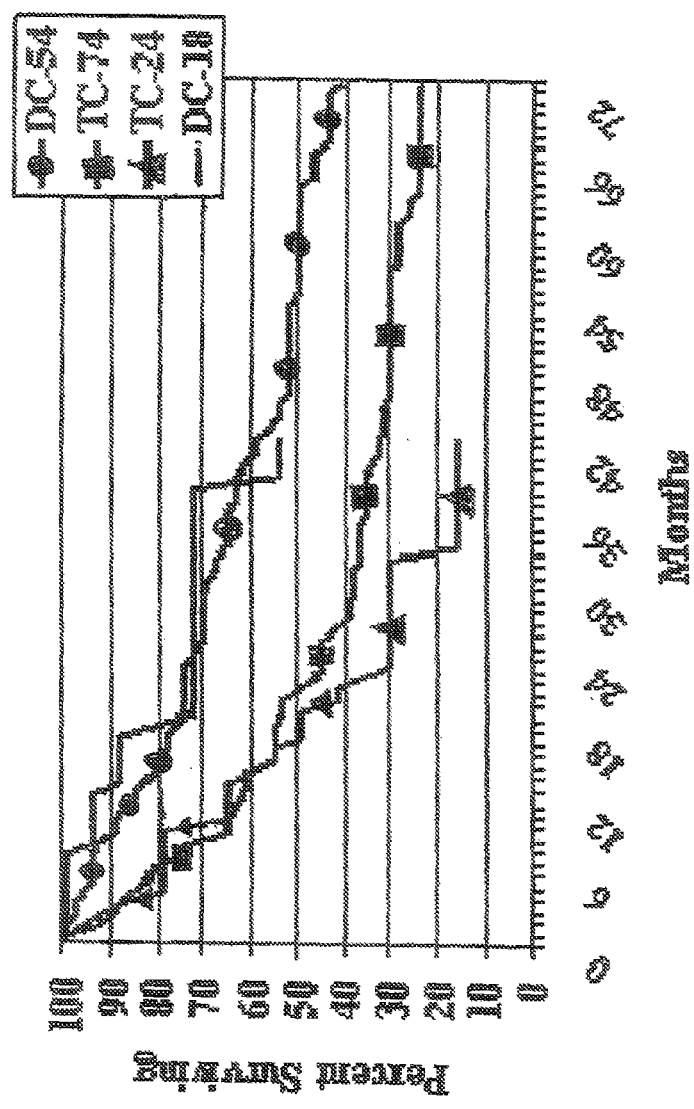

FIG. 13 shows survival curves from three trials. The plot (Kaplan-Meier plot) is a stepwise curve showing the percent of study subjects surviving during the course of clinical trials. The groups are designated DC-54 (solid circle); TC-74 (solid square); TC-24 (solid triangles); and DC-18 (line). Poorest survival occurred with TC-24. The next poorest survival was with TC-74. TC-24 refers to a vaccine of tumor cells in a study involving 24 subjects.

Figure 14:
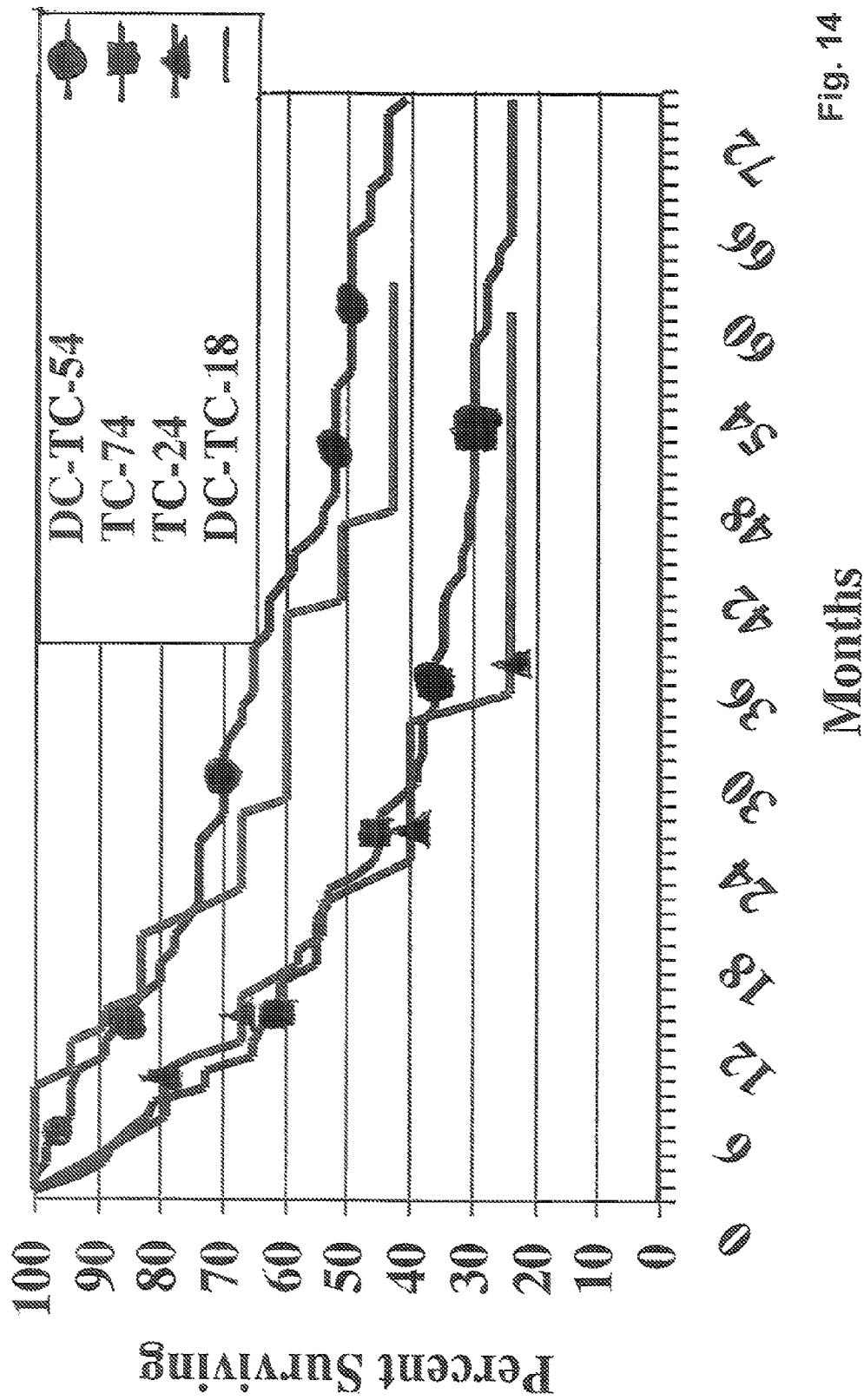

FIG. 14 shows survival curves from three trials. The trials are the same clinical trials as those disclosed in FIG. 13, but with additional data acquired from later time points.

FURTHER DESCRIPTION

Autologous Dendritic Cell Generation

Dendritic cells were generated by plastic adherence method of ficoled apheresis products (Choi, et al. (1998) Clin. Cancer Res. 4:2709-2716; Luft, et al. (1998) Exp. Hematol. 26:489-500; Cornforth, et al. (2011) Cancer Immunol. Immunother. 60:123-131), in antibiotic-free AIM-V medium (Invitrogen, Grand Island, N.Y.) supplemented with 1,000 IU/mL each of IL-4 (CellGenix, Freisberg, Germany) and GM-CSF (Berlex, Seattle, Wash.) (DC medium). The flasks were then cultivated for 6 days prior to loading with IFN-gamma treated, irradiated autologous tumor cells.

IFN-Gamma Autologous Tumor Cell Line Generation and Preparation of Pharmaceutical Pure tumor cells were generated according to Cornforth, et al. (Cornforth, et al. (2011) Cancer Immunol. Immunother. 60:123-131; Dillman, et al. (1993) J. Immunother. Emphasis Tumor Immunol. 14:65-69; Dillman, et al. (2000) Cancer Biother. Radiopharm. 15:161-168). The tumor cells were then incubated with 1,000 U/mL of interferon-gamma (InterMune, Brisbane, Calif.) for 72 h, irradiated with 100Gy from a cesium source and cryopreserved (Selvan, et al. (2007) Int. J. Cancer 122:1374-1383; Selvan, et al. (2010) Melanoma Res. 20:280-292). The IFN-gamma treated and irradiated tumor cells were recovered from cryopreservation, washed with phosphate buffered saline (PBS), and then added to the cultivated dendritic cells (DCs) and then incubated for about 24 h. The antigen-loaded DCs were harvested by gentle scraping with a rubber policeman and cryopreserved. Aliquots of IFN-gamma treated or untreated tumor cells and loaded DCs were obtained for flow cytometry evaluation and trypan-blue exclusion assay.

Staging of Cutaneous Melanoma

The pharmaceutical or reagent of the disclosure can be administered to melanoma patients, where melanoma is diagnosed at Stage I, Stage II, Stage III, or Stage IV (Mohr, et al (2009) Ann. Oncology (Suppl. 6) vi14-vi21). Stage I, for example, refers to patients with primary melanomas without evidence of regional or distant metastasis. Stage II includes patients without evidence of lymphatic disease or distant metastases, where the patients are further characterized, e.g., by lesions greater than 1 mm and less than or equal to 2 mm thick with ulceration of the overlying epithelium, or by lesions greater than 2 mm and less than or equal to 4 mm thick with epithelial ulceration. Stage III melanoma includes lesions with pathologically documented involvement of regional lymph nodes or in-transit or satellite metastases, where patients may have, e.g., one, two, three, or four or more affected lymph nodes. Stage IV melanoma is defined by the presence of distant metastases, where the metastasis is located only in distant skin, subcutaneous tissues, or lymph nodes, where the metastasis involves lung metastases, or where the metastasis involves all other visceral sites.

The disclosure encompasses methods for administration that are preventative, that is, for use with subjects not yet or never diagnosed with a melanoma. What is encompassed are methods for administration where a subject had earlier been diagnosed with a melanoma, and had earlier been successfully treated to eradicate the melanma (or had experienced a spontaneous complete remission), and where following eradication the administration is used preventatively.

Tumor Antigens

Without implying any limitation, melanoma cells of the disclosure express one or more of Mage, Mart-1, Mel-5, HMB45, S100, or tyrosinase (Dillman, et al. (2011) Cancer Biotherapy Radiopharmaceuticals 26:407-415). In one aspect, detection of tumor antigen uses cells that were not exposed to IFN-gamma while, in another aspect, detection of tumor antigen is conducted on cells that were treated with IFN-gamma (see, e.g., Cornforth, et al. (2011) Cancer Biotherapy Radiopharmaceuticals 26:345-351). What is encompassed are melanoma cells expressing one or more melanoma antigens, or compositions comprising one or more isolated melanoma antigens, as disclosed by US2007/0207171 of Dubensky, et al, which is incorporated herein by reference in its entirety.

Measuring Apoptosis

Apoptosis can be detected or measured with a number of reagents, e.g., fluorochrome-labeled annexin, by staining with dyes such as propidium iodide and 7-aminoactinomycin D (7-AAD), by determining loss of mitochondrial inner membrane potential, by measuring activation or cleavage of caspases. See, e.g., George, et al. (2004) Cytometry Part A. 59A:237-245. An early event in apoptosis is exposure of phosphatidyl serine on the outer surface of the plasma membrane, which can be detected by fluorochrome-labeled annexin. The available methods can distinguish between live cells, necrotic cells, early apoptotic cells, and late apoptotic cells. The disclosure uses melanoma cells that are not apoptotic by 7-ADD assay, not apoptotic by annexin V assay, not apoptotic by an assay for apoptosis after IFN-gamma treatment (Dillman, et al. (2011) Cancer Biotherapy Radiopharmaceuticals 26:407-415), or not apoptotic by one or more of the biomarkers Bcl-2, caspase-3, P53, or survivin (Karam, et al. (2007) Lancet Oncol. 8:128-136). The pharmaceutical compositions, reagents, and related methods, of the disclosure exclude IFN-gamma-treated melanoma cells that are apoptotic, where apoptosis is determined, e.g., according to U.S. Pat. No. 7,544,465 issued to Herlyn, et al; U.S. Pat. No. 7,714,109 issued to Thorpe, et al, which are incorporated herein by reference.

Measuring Autophagy

Autophagy is a naturally occurring process that is used for the degradation of many proteins and some organelles. Autophagy mediates protein and organelle turnover, starvation response, cell differentiation, cell death, and so on. Microtubule-associated protein light chain 3 (LC3) is to monitor autophagy. In one approach, autophagy can be detected by measuring the conversion of LC3, which involves conversion of LC3-I to LC3-II. The amount of LC3-II is correlated with the number of autophagosomes. In detail, LC3 is cytosolic and soluble, while LC3-II is present on membranes. LC3-II has a greater molecular weight because it is conjugated with a lipid. LC3 processing can be measured, e.g., by western blots, while autophagy, autophagic vesicles, and autophagosomes, can be measured by microscopy. Autophagy can be quantitated, e.g., by detecting processed LC3-II, by the ratio between early to late autophagic compartments, or by autophagic volume. See, (Mizushima and Yoshimori (2007) Autophagy 3:542-546:634-641; Tanida, et al. (2008) Methods Mol. Biol. 445:77-88; Eng, et al. (2010) Autophagy 6:634-641). In one aspect, the present disclosure uses autophagy as a screening tool, for selecting appropriate autophagic cancer cells, where the cells can be selected according to occurrence of autophagy in one or more particular stages. These autophagy stages include: (1) sequestering of cytosolic compartments by the autophagosome, (2) fusion of the autophagosome with the lysosome to form the autolysosome, and (3) degradation of the autophagosomal contents by proteases within the lysosome. In another aspect, the present disclosure includes mainly cells displaying the first stage, mainly the second stage, mainly the third stage, mainly the first and second stage, mainly the second and third stage, or mainly cells displaying all three stages. In yet another aspect, the disclosure comprises cells displaying the first stage, the second stage, the third stage, the first and second, the second and third stage, or cells displaying all three stages.

Interferon-Gamma (IFN-Gamma) Signaling

IFN-gamma (type II interferon) signaling depends on expression of a number of genes, e.g., IFN-gamma receptor, STAT1, STAT2, STAT1 homodimers, STAT1/STAT2 heterodimers, IRF-1, GAS, and IRF-E. Studies have shown that IFN-gamma signaling is dependent on IFN-gamma receptor (IFNGR1 chain; IFNGR2 chain). Low expression of IFNGR on the cell surface can block some aspects of IFN-gamma signaling (Schroder, et al. (2004) J. Leukocyte boil. 75:163-189). In one aspect, the present disclosure excludes using cancer cells that show low surface expression of IFNGR. In another aspect, the present disclosure screens cancer cells for those that express the STAT1 homodimer, uses these cells, and substantially excludes cells that do not express STAT1 homodimer. In yet another aspect, the disclosure contemplates screening cells for those with STAT1 phosphorylation (serine-727). What is also contemplated, is excluding cancer cells from patients having loss of function mutations in the STAT1 gene (see, e.g., Dupuis, et al. (2001) Science 293:300-303; Schroder, et al. (2004) J. Leukoc. Biol. 75:163-189). The following concerns the IRF gene family. IRF-1, IRF-2, and IRF-9, all participate in IFN-gamma signaling. The disclosure embraces using cancer cells that express one or more of these IRF gene family genes, or excluding cancer cells that do not express one or more of these genes.

IFN-Gamma Responsive Genes

The present disclosure embraces biologic material, compositions, reagents, and methods that require using a melanoma cell, or pre-neoplastic melanoma cell, that responds to IFN-gamma. The melanoma cell can be identified, distinguished, and selected, by an assay for the expression of one or more IFN-gamma-responsive genes. A number of IFN-gamma-responsive genes have been identified (see, e.g., Halonen, et al. (2006) J. Neuroimmunol. 175:19-30; MacMicking (2004) 11:601-609; Boehm, et al. (1997) 15:749-795). Said assay can involve removing one or more melanoma cells from the patient, culturing the cell in the presence and absence of added IFN-gamma, and determining responsiveness to IFN-gamma. In the assay, IFN-gamma induced gene expression can be detected by assays sensitive to binding of a transcription factor to the promoter of an IFN-gamma induced gene, to expression of mRNA from an IFN-gamma induced gene, to expressed polypeptide, and the like. The IFN-gamma response gene can include, e.g., a gene used for immune response, encoding a transcription factor, a transport protein, an apoptosis gene, a gene used for cell growth or maintenance, a gene used for lipid metabolism, a gene that mediates endocytosis or exocytosis, an intracellular signaling gene, a glucose metabolism gene, a cell adhesion gene, as well as genes without an established function.

In one aspect, the disclosure excludes melanoma cells that, with IFN-gamma treatment, show reduced expression of MHC class II, show no detectable change in expression of MHC class II, show an increase of MHC class II expression of 10% or less, show an increase in MHC class II expression of 15% or less, show an increase in MHC class II expression of 20% or less, 25% or less, 30% or less, 40% or less, 50% or less, and the like. In one aspect, the value for percentage refers to the average expression value for the population of melanoma cells, residing in a biopsy or part of a biopsy, from a given subject or patient.

Non-Limiting Lists of IFN-Gamma Inducible Genes for Use in Screening for IFN-Gamma Responsive Cancer Cells ab000677, JAB/SOCS1; m63961, IFN-gamma inducible protein (mag-1); m35590, Macrophage inflammatory protein 1-β; m19681, MCP-1 (JE); y07711, zyxin; M34815, Monokine induced by IFN-gamma (MIG); m33266, Interferon inducible protein 10 (IP-10); U44731, Purine nucleotide binding protein; U88328, Sup. of cytokine signalling-3 (SOCS-3); M21065, Interferon regulatory factor 1; M63630, GTP binding protein (IRG-47); U19119, G-protein-like LRG-47; L27990, Ro protein; M31419, 204 interferon-activatable protein; af022371, Interferon-inducible protein 203; U28404, MIP-1 alpha receptor; U43085, Glucocorticoid-attenuated response 39; x56123, Talin; m31419, 204 interferon-activatable protein; U53219, GTPase IGTP; I38444, T-cell specific protein; M31418, 202 interferon-activatable protein; d38417, Arylhydrocarbon receptor; m26071, Tissue factor (mtf); D13759, Cot proto-oncogene; M18194, Fibronectin; u59463, ICH-3; M13945, pim-1 proto-oncogene; L20450, DNA-binding protein (see, Gil, et al. (2001) Proc. Natl. Acad. Sci 98:6680-6685). The disclosure encompasses use of the IFN-gamma induced gene, CIITA (see, e.g., Chan, et al. (2010) J. Leukocyte Biol. 88:303-311; Kwon, et al (2007) Mol. Immunol. 44:2841-2849).

The present disclosure embraces measuring expression of one or more of the following IFN-gamma inducible genes, as a screening procedure for qualifying or selecting patients for administering a pharmaceutical. The genes include, (gene 1) FCGR1A, (gene 2) IL6R, (gene 3) CXCL9, (gene 4) CLCSF14, (gene 5) UBD, (gene 6) C/EBPalpha, and (gene 7) MHC2TA (CIITA) (see, Waddell, et al. (2010) PLoS ONE 5:e9753). Also embraced are use of specific clusters of these genes, in the qualifying procedure, such as, genes 1 and 2, 2 and 3, 3 and 4, 4 and 5, 5 and 6, 6 and 7, 1 and 3, 1 and 4, 1 and 5, 1 and 6, 1 and 7, 2 and 4, 2 and 5, 2 and 6, 2 and 7, 3 and 5, 3 and 6, 3 and 7, 4 and 6, 4 and 7, 5, and 7, and well as combinations of three genes, e.g., 1, 2, 3; or 3, 4, 5; or 4, 5, 6; or 5, 6, 7; or 1, 3, 4; or 1, 3, 5, or 1, 3, 6, or 1, 3, 7; or 1, 2, 4; or 1, 2, 5; or 1, 2, 6; or 1, 2, 7; and the like. (These gene numbers are arbitrary.)

What is excluded is a population of melanoma cells that is less than 90% are autophagic, less than 80% are autophagic, less than 70% are autophagic, less than 60% are autophagic, less than 50% are autophagic, less than 40% are autophagic, and the like.

What is excluded is a population of melanoma cells where, that is less than 90% are non-apoptotic, less than 80% are non-apoptotic, less than 70% are non-apoptotic, less than 60% are non-apoptotic, less than 50% are non-apoptotic, less than 40% are non-apoptotic, and the like.

What is excluded is a population of melanoma cells that is less than 90% are non-adherent, less than 80% are non-adherent, less than 70% are non-adherent, less than 60% are non-adherent, less than 50% are non-adherent, less than 40% are non-adherent, and the like.

Measuring Expression of MHC Class II

Expression of MHC class II can be measured, for example, using antibodies or nucleic acid probes that are specific for MHC class II gene products. These MHC class II gene products include HLA-DPA1, HLA-DPB1, HLA-DQA1, HLA-DQB1, HLA-DRA, HLA-DRB1, as well as HLA-DM and HLA-DO (see, e.g., Apostolopoulos, et al. (2008) Human Vaccines 4:400-409).

For example, the present disclosure encompasses reagents, methods of treatment, and methods of diagnosis, that require the melanoma cells to express STAT1 and STAT2, to have an active STAT1-signaling pathway, to have an active STAT2-signaling pathway, or to have active STAT1 and STAT2-signaling pathways.

The disclosure provides a pharmaceutical composition or pharmaceutical reagent, related methods of administration, and methods of treatment, that result in survival data with a hazard ratio (HR) of less than 1.0, HR less than 0.9, HR less than 0.8, HR less than 0.7, HR less than 0.6, HR less than 0.5, HR less than 0.4, HR less than 0.3, and the like. The disclosure results in overall survival data, progression-free survival data, time to progression data, and so on. What is also provided is 6-month PFS of at least 40%, at least 50%, at least 60%, at least 70%, at least 75%, at least 80%, at least 85%, at least 90%, at least 95%, and so on. Moreover, what is provided is 6-month overall survival of at least 40%, at least 50%, at least 60%, at least 70%, at least 75%, at least 80%, at least 85%, at least 90%, at least 95%, and so on. Additionally, what is provided is 1-year (or 2-year) PFS of at least 40%, at least 50%, at least 60%, at least 70%, at least 75%, at least 80%, at least 85%, at least 90%, at least 95%, and so on. Moreover, what is provided is 1-year (or 2-year) overall survival of at least 40%, at least 50%, at least 60%, at least 70%, at least 75%, at least 80%, at least 85%, at least 90%, at least 95%, and so on (see, e.g., U.S. Dept. of Health and Human Services. Food and Drug Administration. Guidance for Industry. Clinical trial endpoints for the approval of cancer drugs and biologics (April 2005)).

IFN-Gamma and the Induction of Autophagy

Induction of autophagy after IFN-gamma treatment, as measured by increases in the expression of major histocompatibility class II complexes, can be used to determine response to systemic IFN-gamma treatment. If biopsied melanoma tumor cells, upon exposure to IFN-gamma in culture, undergo autophagy but not apoptosis, this indicates that these patients will respond favorably to systemic IFN-gamma treatment. Additionally, if successful cell lines are established from the biopsies, that patient would also benefit from cell-therapy products prepared from IFN-gamma treated purified tumor cells lines that are from autophagic but non-apoptotic adherent populations.

The disclosure embraces isolating and characterizing major histocompatiability complexes isolated from autophagic, non-apoptotic cells collected from tumor cell lines treated with interferon-gamma. Major histocompatibility complexes contain antigens specific for $CD4^+$ T cells and have been associated with antibody mediated immune responses. The complexes would represent a large repertoire of antigens would not be present in non-autophagic cells due to the action of lysosomal mediated antigen processing induced in autophagic cells.

Non-apoptotic, autophagic tumor cells generated from IFN-gamma treated cell lines can be fused with dendritic cells to enhance the antigen presentation due to the high levels of major histocompatability complexes on the surface of the autophagic tumor cells. This process would yield a novel cellular product generated from the fusion of the two cell types.

The process of induction of autophagy in response to IFN-gamma may be induced in a manner that does not result in apoptosis. By combining the treatment of tumor cells with caspase inhibitors and interferon gamma, the process of cell death (and ultimately the formation of tolergeneic apoptotic cells) can be blocked without inhibiting the induction of autophagy or the increase in major histocompatibility class II complexes.

Procedure to Eliminate Apoptotic Cells, while Retaining Viable Autophagic Cells

Studies of melanoma demonstrated a correlation between the presence of apoptotic cells and poor survival in a clinical trial (Cornforth, et al. (2011) Cancer Immunol. Immunother. 60:123-131; Dillman, et al. (2011) Cancer Biother. Radiopharmaceuticals 26:407-415). The following study investigated the induction of autophagy, apoptosis and MHC class II molecules after IFN-gamma treatment of melanoma tumor cells in vitro.

The methodology of the study was as follows. Autologous and model melanoma tumor cell lines were incubated with 1000 IU/mL of IFN-gamma for 72 hours prior to assaying for autophagy, apoptosis and MHC class II expression. Autophagy was detected by immunoblotting with antibodies against LC3 II and by flow cytometry with Enzo's CytoID® Autophagy Detection Kit. Apoptosis and MHC class II induction were assayed by flow cytometry using 7-AAD and annexin-V staining and antibodies against MHC class II, respectively.

The results from the study demonstrated that IFN-gamma induces both autophagic and apoptotic cell populations in melanoma cell lines. The apoptotic population was predominantly found in the non-adherent population while the autophagic cells remained adherent to the flask. Blocking of autophagy with the inhibitor 3-methyladenine (3-MA) inhibits the induction of MHC class II positive cells in response to IFN-gamma (39.4% IFN-gamma vs. 10.0% IFN-gamma+3-MA). Inhibition of caspase activity with the pan caspase inhibitor Z-VAD prevents apoptosis but does not perturb autophagy in IFN-gamma treated cells (2.75±0.15 IFN-gamma vs. 3.04±0.27 IFN-gamma+Z-VAD, fold change). To conclude, induction of apoptosis is associated with reduced levels of autophagy and MHC class II induction. This disclosure provides method or procedure to eliminate apoptotic cells while retaining viable autophagic cells after IFN-gamma treatment can enhance the effectiveness of this type of cell-based immunotherapy.

IFN-gamma has been associated with suppression of immune response against tumors (see, e.g., Hallermalm (2008) J. Immunol. 180:3766-3774; Romieu-Mourez (2010) Cancer Res. 70:7742-7747; Lee (2005) Clinical Cancer Res. 11:107-112).

A tumor can be a heterogeneous population of more or less differentiated cells. IFN-gamma treatment of melanoma cells of a tumor can act on some of the more differentiated cells, that are more susceptible to apoptosis. By eliminating these cells from the antigen source, the result can be loss of some effect on the tumor bulk following vaccination, translated by slow or no apparent regression of tumor size. Studies have shown that apoptotic cells do not activate dendritic cells (Sauter (2000) J. Exp. Med. 191:423-434).

IFN-gamma may act to skew monocyte differentiation from DCs to macrophages. The amount of IFN-gamma in the preparation may influence the incomplete differentiation of DCs by skewing the phenotype to the less specialized macrophages.

IFN-gamma may be used to enhance the MHC Class II molecules, and have a direct presentation to the T cells. However, the co-induction of II protein (Calprotectin) with MHC Class II molecules prevents the presentation of endogenous tumor antigens from MHC Class II molecules.

Materials and Methods from First Study

Autologous Dendritic Cell Generation

Dendritic cells were generated by plastic adherence method as previously described (Choi (1998) Clin. Cancer Res. 4:2709-2716; Luft (1998) Exp. Hematol. 26:489-500). Briefly, autologous apheresis product was subjected to ficoll-hypaque (GE Healthcare, Buckinghamshire, United Kingdom) density gradient separation. The resulting peripheral blood mononuclear cells were placed in antibiotic-free AIM-V medium (Invitrogen, Grand Island, N.Y.) supplemented with 1,000 IU/mL each of IL-4 (CellGenix, Freisberg, Germany) and GM-CSF (Berlex, Seattle, Wash.) (DC medium) at $15 \times 10^8$ cells/mL in cell cultivation flasks (Corning-Costar, Corning, N.Y.). After one hour incubation, the non-adherent population was discarded and fresh DC medium was added to the flasks. The following morning, the non-adherent cells were discarded, the flasks were washed once with ambient temperature PBS, and fresh DC medium was added. The flasks were then cultivated for 6 days at which time flow cytometry evaluation is performed to determine the percentage and phenotype of DC generated by this approach (pre-load DC).

Autologous Tumor Cell Line Generation

Pure tumor cells generated and characterized as previously reported were expanded to 200 million cells and then incubated with 1000 IU/mL of IFN-gamma (InterMune, Brisbane, Calif.) for 72 hours in 15% FBS/ECS in RPMI (complete medium), irradiated with 100 Gy from a cesium source and cryopreserved as previously described (Choi (1998) Clin. Cancer Res. 4:2709-2716; Luft (1998) Exp. Hematol. 26:489-500; Dillman (1993) J. Immunother. Emphasis Tumor Immunol. 14:65-69). The IFN-gamma treated and irradiated tumor cells were recovered from cryopreservation, washed 3× with PBS, and then added to the in vitro cultivated DC and incubated for ~24 hours. The antigen loaded DC were harvested by gentle scraping with a rubber policeman and cryopreserved at equal amounts in 9-11 aliquots. An aliquot of cells was obtained for flow cytometry evaluation which represents the post-loaded DC cells.

Flow Cytometry

Phenotypic characterization of the dendritic cell populations were performed using monoclonal antibodies against surface markers obtained from BD Pharmingen San Diego, Calif.: anti-MHC class II conjugated to PerCp, anti CD11c conjugated to APC, anti-CD80, anti-CD83, anti-CD86 conjugated to PE. Isotype controls were used to determine percent positive cells. Flow cytometry of tumor cells was conducted using antibodies against MHC class I and II conjugated to FITC, annexin-V-PE and 7-amino-actinomycin D (7-AAD) from BD Pharmingen. CaliBRITE flow cytometry calibration (BD Pharmingen) was used prior to each run and the same instrument settings were used throughout the collection of flow cytometric data.

Immunoblot Assays

Cytoplasmic cell lysates were prepared with Mammalian Protein Extraction Reagent (Thermo Scientific, Rockford, Ill.) plus protease inhibitor cocktail (Roche, Indianapolis, Ind.) at 10,000 cells/uL on ice. Approximately 25 uLs/lane of cell lysates were separated on 12.5% tris-glycine gels, transferred to PVDF membrane and probed with antibodies against the following: calreticulin (MBL, Woburn, Mass.), Hsp-60, Hsp-70, Hsp-90 (R&D Systems, Minneapolis, Minn.), HMBG-1 (Cell Signaling, Danvers, Mass.), ICAM-1 (Santa Cruz Biotech, Santa Cruz, Calif.), Mel-4, Mart-1 (Signet, Emeryville, Calif.), tyrosinase (Upstate, Lake Placid, N.Y.) and GADPH (Calbiochem, Darmstadt, Germany).

Immunohistochemistry

Expression of a panel antigens by melanoma lines were determined using immunocytochemical procedure. Cells were cultured in 8-chamber culture slides (Thermo Fisher, Rochester, N.Y.) in the presence or absence of 1000 IU/mL IFN-gamma. After 72 hours, the cells were washed 3 times with 1× Phosphate Buffered Saline (PBS) and fixed in cold acetone. After blocking endogenous peroxidase, cells were incubated with appropriate primary antibodies against the antigens listed. Immunohistochemistry was performed using biotinylated anitmouse or rabbit immunoglobulins, Super Sensitive enzyme-conjugated streptavidin labeling and horse radish peroxidase chromogen, and substrate kits (Biogenex, San Ramon, Calif.). The reactivity of the following anti-human polyclonal or monoclonal antibodies was investigated with isotype matched control antibody: S-100 and HMB-45 (Biogenex, San Ramon, Calif.), Mel-2, Mel-5, Mart-1 (Signet, Dedham, Mass.), Tyrosinase and Mage-1 (Thermo Scientific, Fremont, Calif.), Melan-A, HLA-class I and HLA-class II (Dako, Denmark).

Statistical Analysis

Student t-test of two-tailed, two samples of equal variance. Significant differences were determined by p value ≤0.05.

Results from the First Study

Cell death was differentially induced in the autologous melanoma tumor cells line in response to incubation with IFN-gamma for 72 hours in complete medium. Trypan-blue dye exclusion assay performed on cells either treated with IFN-gamma or not, revealed a significant trend toward lower viability in the IFN-gamma treated cells (89.1±6.8% vs. 84.9±9.3%, p=0.014, N=47). Analysis of a sample of four autologous melanoma cell lines by flow cytometry for apoptosis induction (FIG. 1A) revealed that melanoma cells are differentially sensitive to the effects of IFN-gamma induced apoptosis with some cells displaying more late apoptosis or 'dead' populations (7-AAD+/Annexin-V+) while others displayed signs of early apoptosis or 'dying' populations (7-MD−/Annexin-V+). The resulting presence of apoptotic cells after IFN-gamma treatment was associated with significant decreases in progression-free and overall survival (Cornforth (2010) Cancer Immunol. Immunother. Resistance to the proapoptotic effects of interferon-gamma on melanoma cells used in patient-specific dendritic cell immunotherapy is associated with improved overall survival). A log-rank test revealed a significant association with lower viability upon IFN-gamma treatment of melanoma tumor cells and overall survival in patients under study.

Lysates from cells that were incubated in the presence or absence of IFN-gamma were subjected to immunoblotting for a variety of molecules that may be important mediators of immunity (FIG. 1B). In the setting of melanoma cells treated with IFN-gamma, heat shock proteins appear to be differentially regulated but remain largely present in the cell preparations, especially in the case of hsp-70. The endoplasmic reticulum protein, calreticulin, and high-mobility group box-1 protein (HMGB-1), appear to be up-regulated in some cases upon treatment with IFN-gamma (FIG. 1B). By contrast, common melanoma antigens (mel-4, Mart-1 and tyrosinase) generally appear to be down regulated by IFN-gamma while ICAM-1, a lymphocyte adhesion molecule associated with sensitivity to lymphocyte mediated cytotoxicity (Hamai (2008) Cancer Res. 68:9854-9864), is significantly up-regulated (FIG. 1C). Indeed, IFN-gamma treated melanoma tumor cells were found to be more sensitive to cytotoxic T lymphocyte (CTL) activity. Additionally, immunohistochemistry of a panel of melanoma associated antigens revealed that IFN-gamma results in the down regulation of antigen expression in many of the antigens examined (Table I).

The use of IFN-gamma results in the up-regulation of the major histocompatibility complexes, class I and class II (Bohn (1998) J. Immunol. 161:897-908). As shown in FIG. 1D, the treatment of autologous melanoma cells with IFN-gamma resulted in the near universal and significant up-regulation of MHC class I ($p=2.8 \times 10^{-8}$) with a median fold induction of $2.91 \pm 1.13$ (95% C.I.). Additionally, the mean fluorescence intensity of MHC class II was also significantly higher but less so (p=0.039) with a median induction of $4.23 \pm 2.66$ (95% C.I.). The level of MHC class II molecules on the surface of the autologous melanoma cells was generally lower than that of the MHC class I molecules but in 70% of the cases the induction was greater than two fold in response to IFN-gamma treatment for the MHC class II molecules due to the low initial level of MHC class II expression. The presence of these molecules on the tumor cells during loading of antigens onto dendritic cells may provide an opportunity for "cross dressing" MHC complexes onto antigen presenting cells (Dolan (2006) J. Immunol. 277:6018-6024, Dolan (2006) J. Immunol. 176:1447-1455).

A set of four representative autologous melanoma cell lines were incubated with IFN-gamma and loaded in equal amounts onto dendritic cells which were then assayed by flow cytometry for the expression of CD80, CD83, CD86 and MHC-class II. The results indicated that a small but appreciable increase in the percent positive population of dendritic cells expressing CD83 was seen upon the loading of the IFN-gamma treated melanoma cells (FIG. 2). Additionally, more unprocessed tumor cells are noted in the CD86 dot plot (upper left quadrant) which resulted in a discernible reduction in the percent CD86 positive population, indicating that IFN-gamma untreated tumor cells were still present. This effect is most likely due to the induction of apoptosis by IFN-gamma, as apoptotic cells are more likely to be phagocytosed by dendritic cells as previously reported.

Figure 2A:
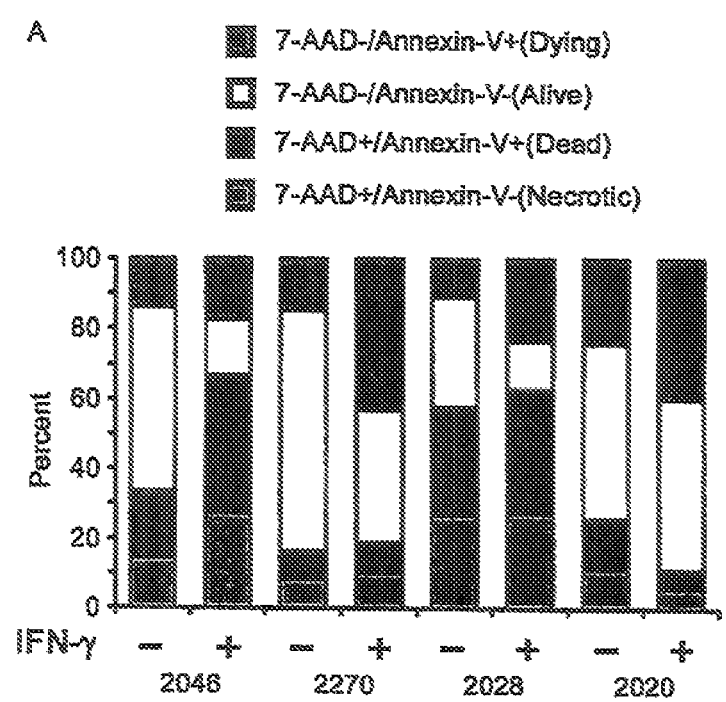
Figure 2B:
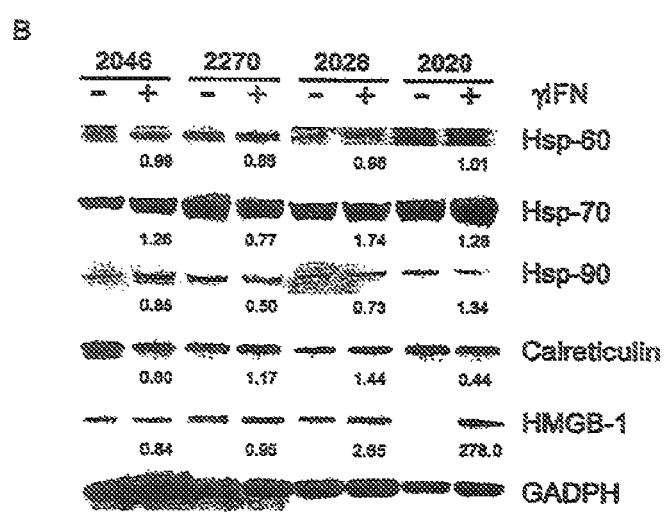
Figure 2C:
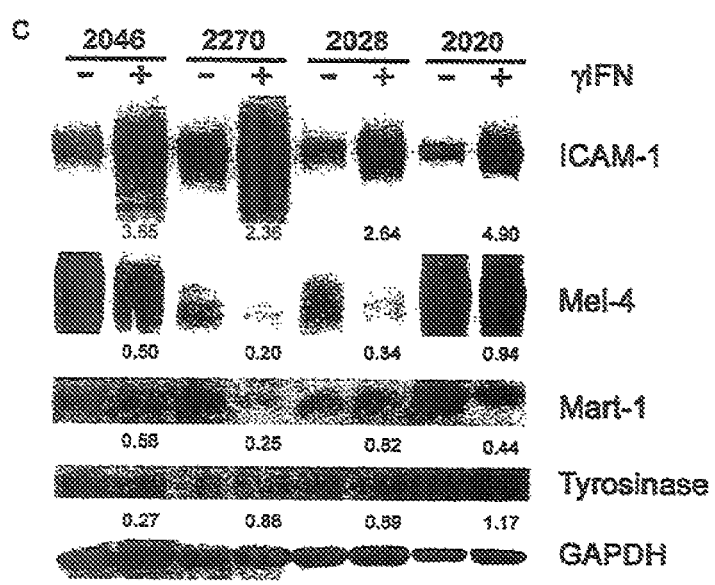
Figure 2D:
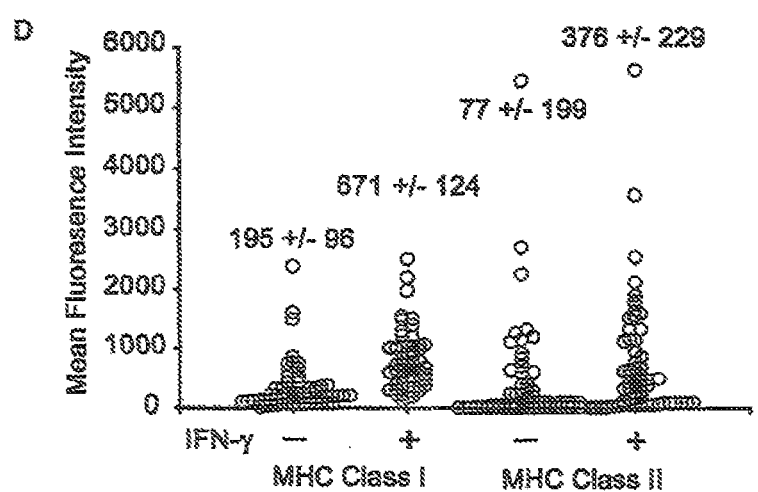
Figure 3A:
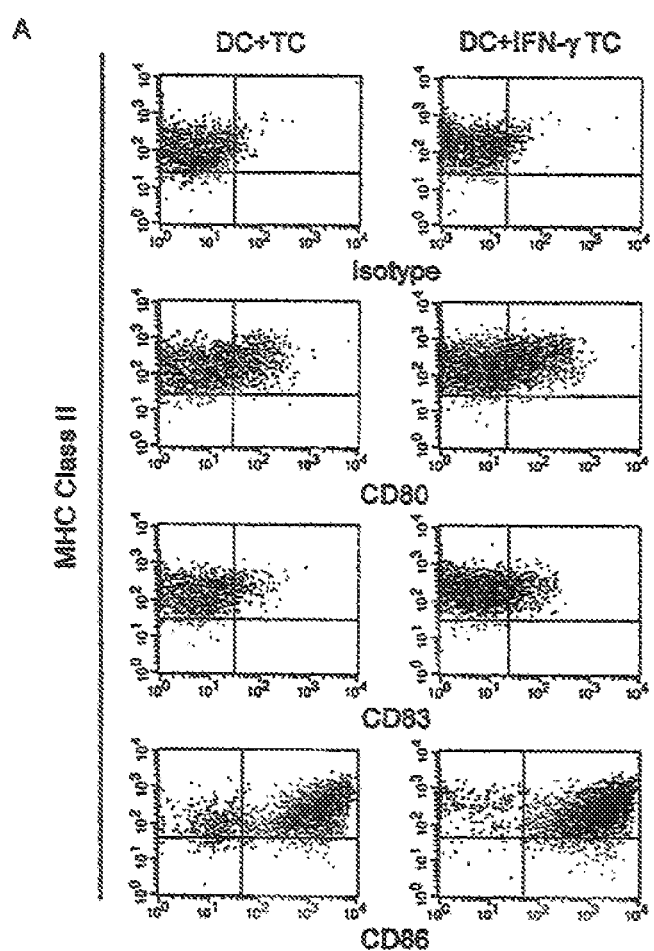
Figure 3B:
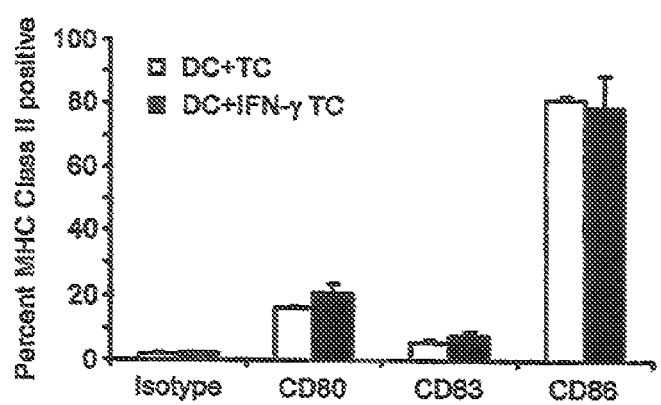
Figure 4A:
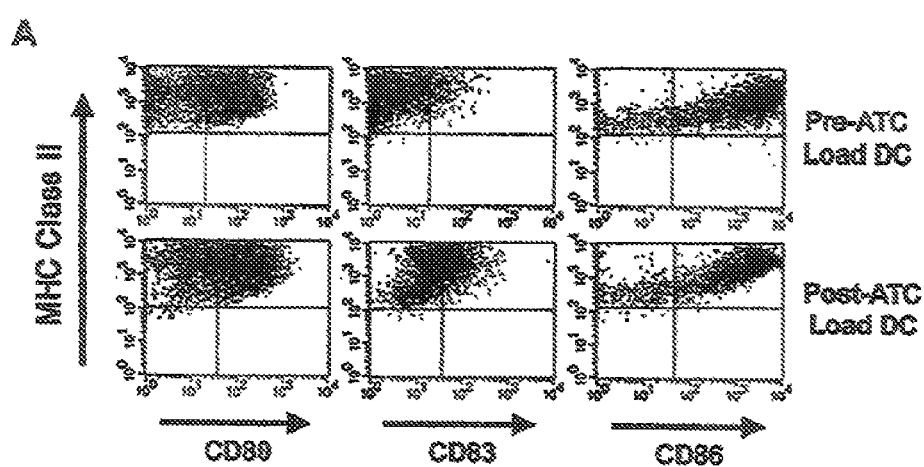
Figure 4B:
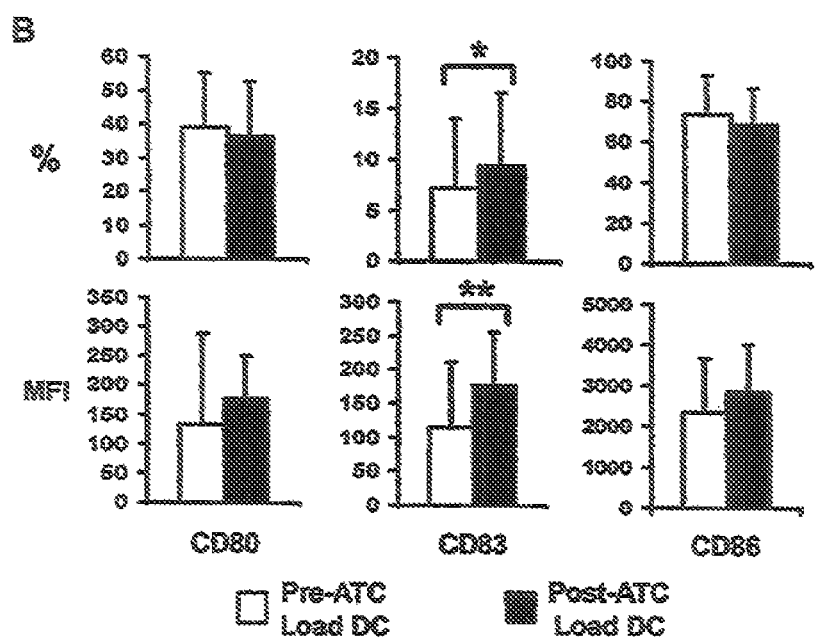
Figure 5A:
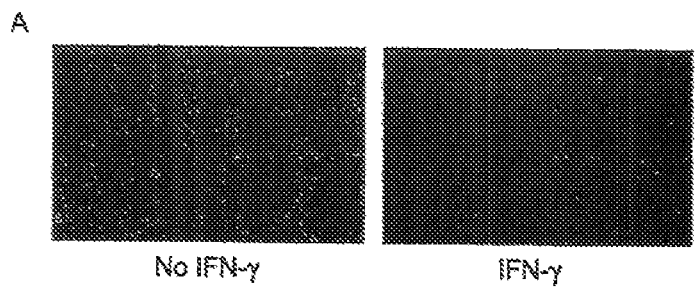
Figure 5B:
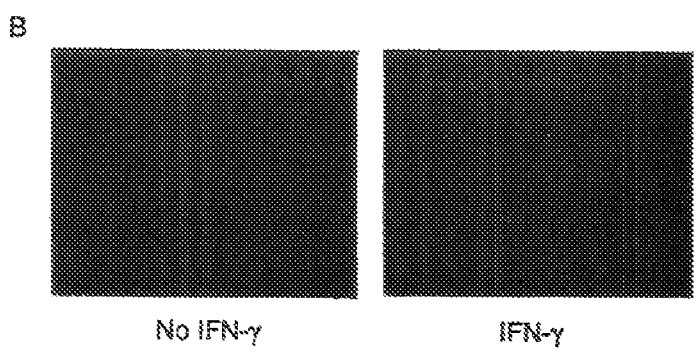
Figure 5C:
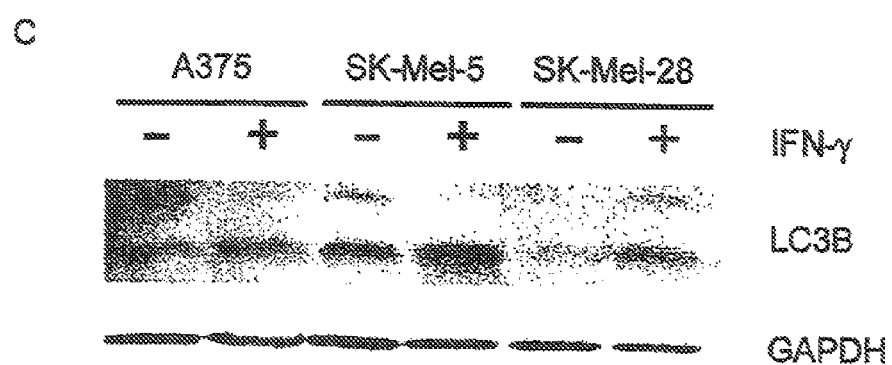
Figure 6A:
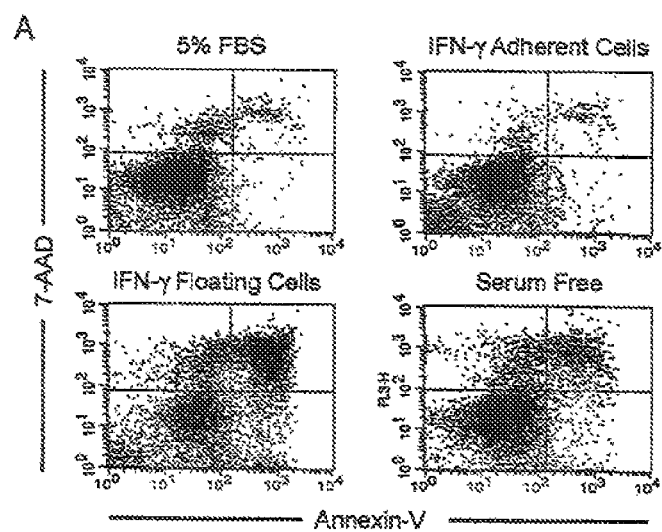
Figure 6B:
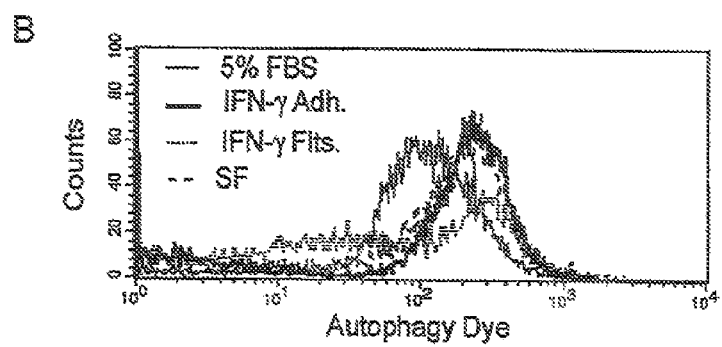
Figure 6C:
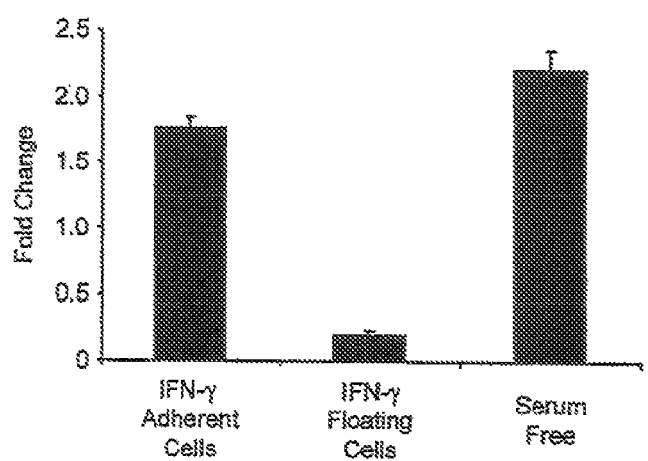
Figure 7A:
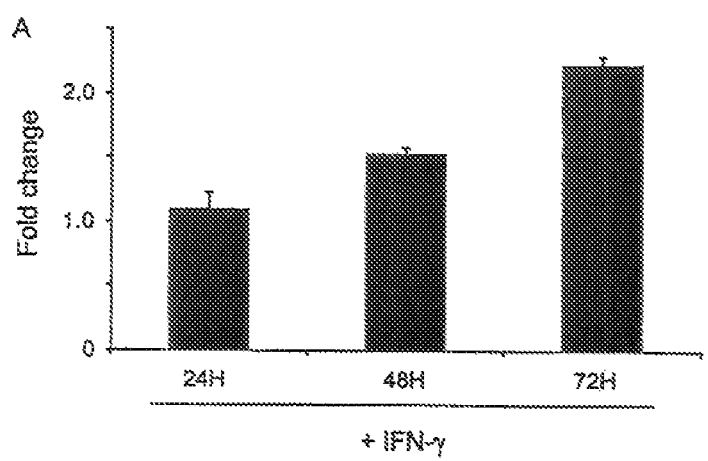
Figure 7B:
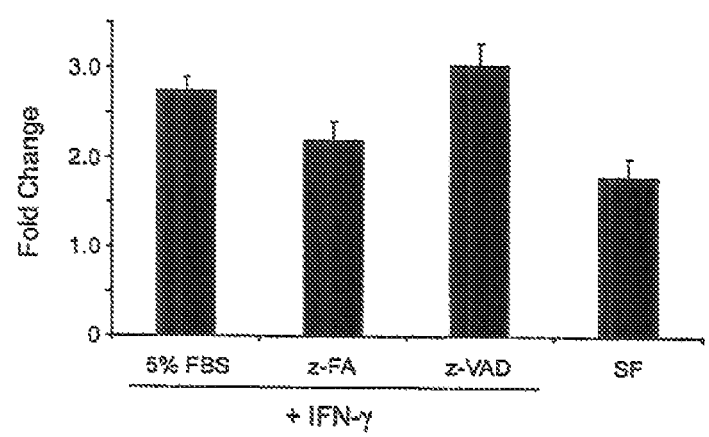
Figure 8:
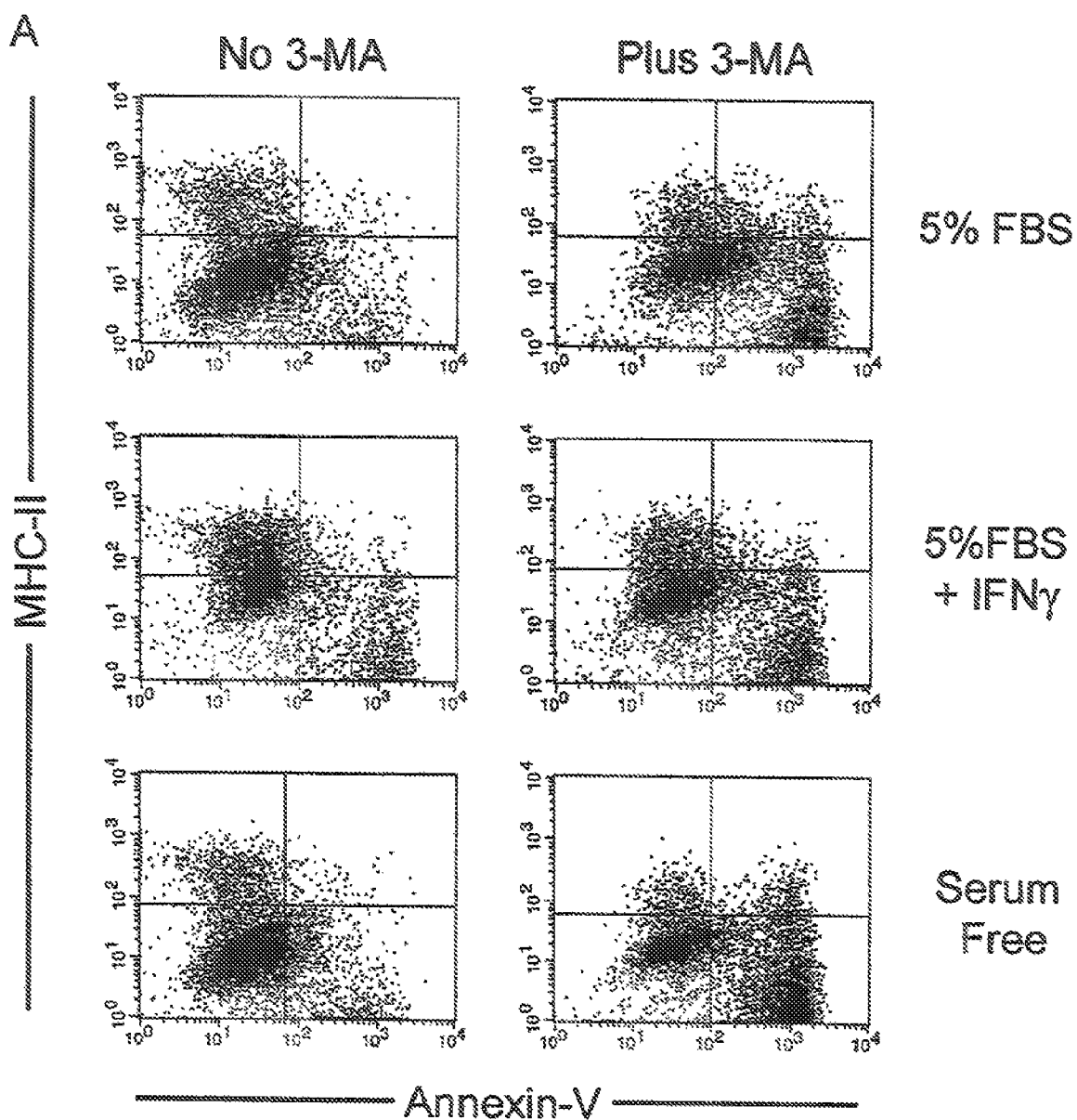
FIG. 8 shows SK-5-Mel cells which were incubated with 1000 IU/mL of IFN-gamma in the presence of 10 uM of the autophagy inhibitor 3-methyladenine (3-MA) for 72 hours. The cells were then harvested and assayed for apoptosis and MHC class II (HLA-DR) expression by flow cytometry.
Figure 9:
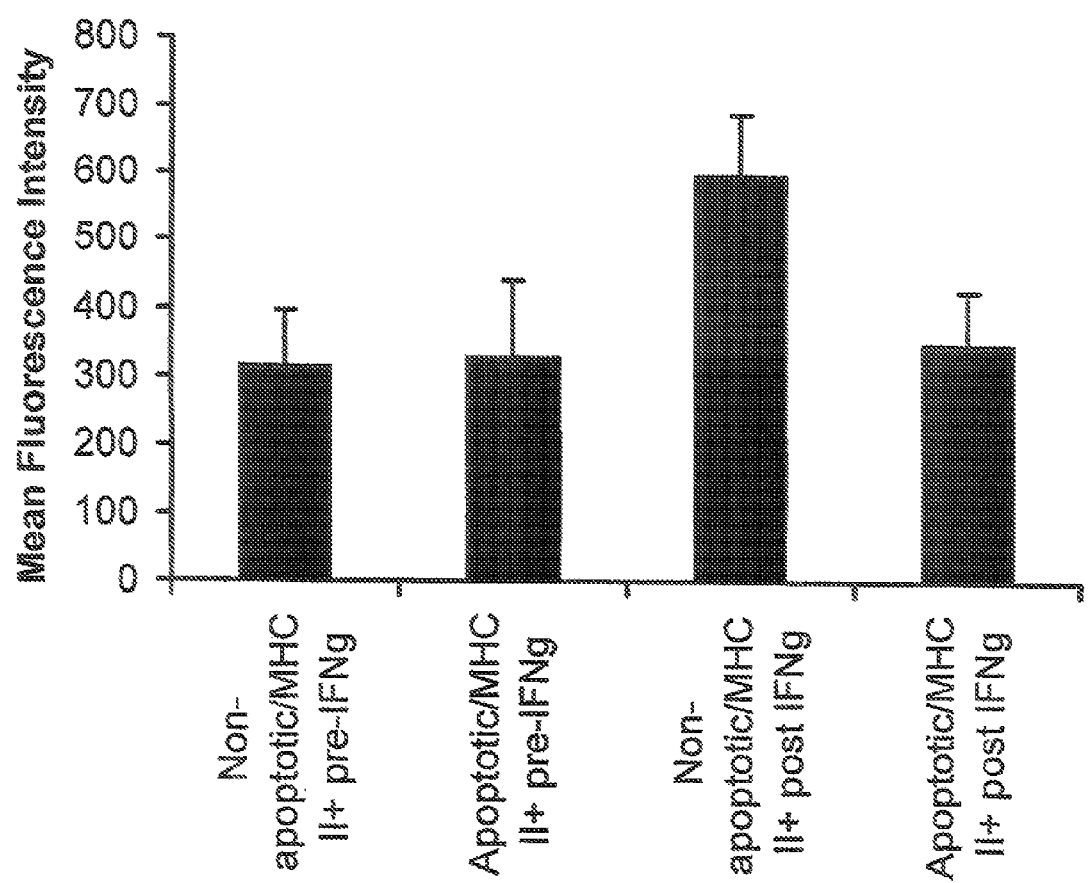
FIG. 9 shows IFN-gamma treated cells from tumor cell lines generated from patient tumor specimens (N=36) were assayed for changes in MHC class II or apoptosis. The data shown are averages of mean fluorescent intensity±SE.
Figure 10:
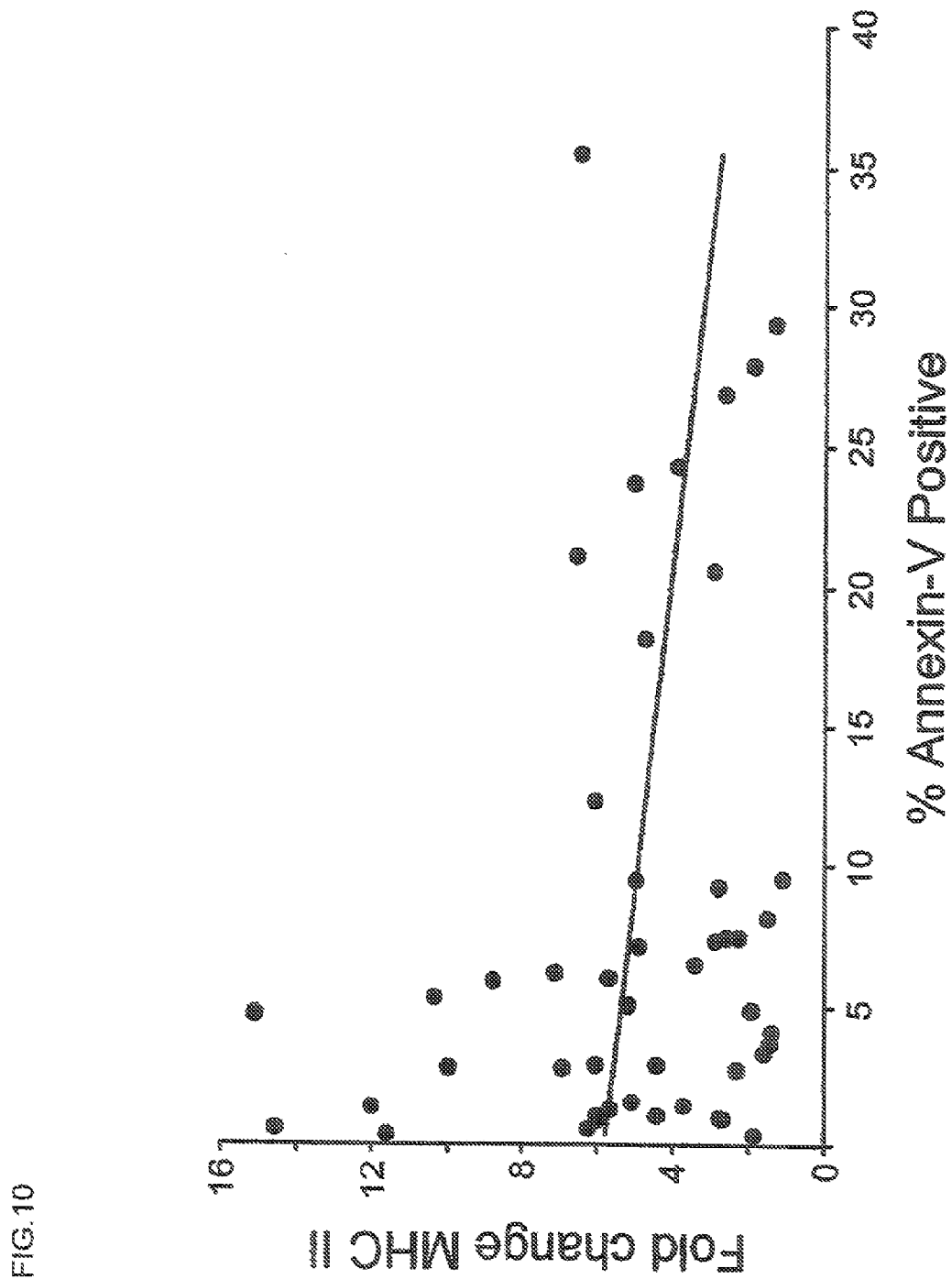
FIG. 10 shows IFN-gamma treated cells that were assayed for MHC class II or apoptosis by flow cytometry from samples used for loading dendritic cells for a patient-specific vaccine immunotherapy (N=54). Fold changes in MHC class II mean fluorescence intensity and percent apoptotic cells (Annexin-V positive) are shown.
Figure 11:
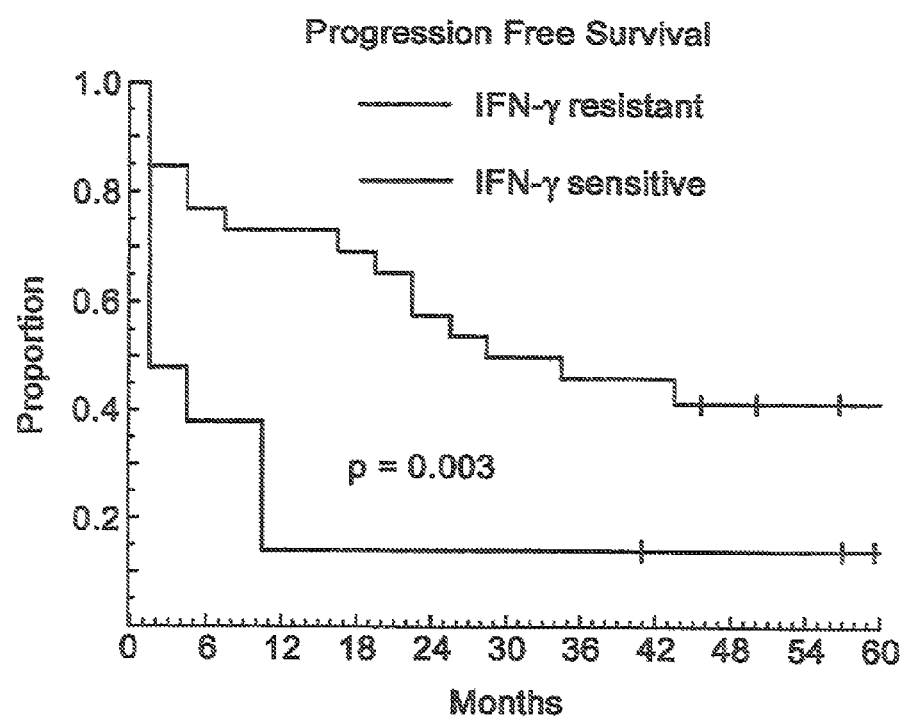
FIG. 11 and FIG. 12 show a correlation between induction of MHC class II and the absence of apoptosis (Interferon-gamma resistant) is associated with better progression-free survival (FIG. 11) and overall survival (FIG. 12) in patients received dendritic cells loaded with autophagic, non-apoptotic interferon-gamma treated tumor cells.
Figure 12:
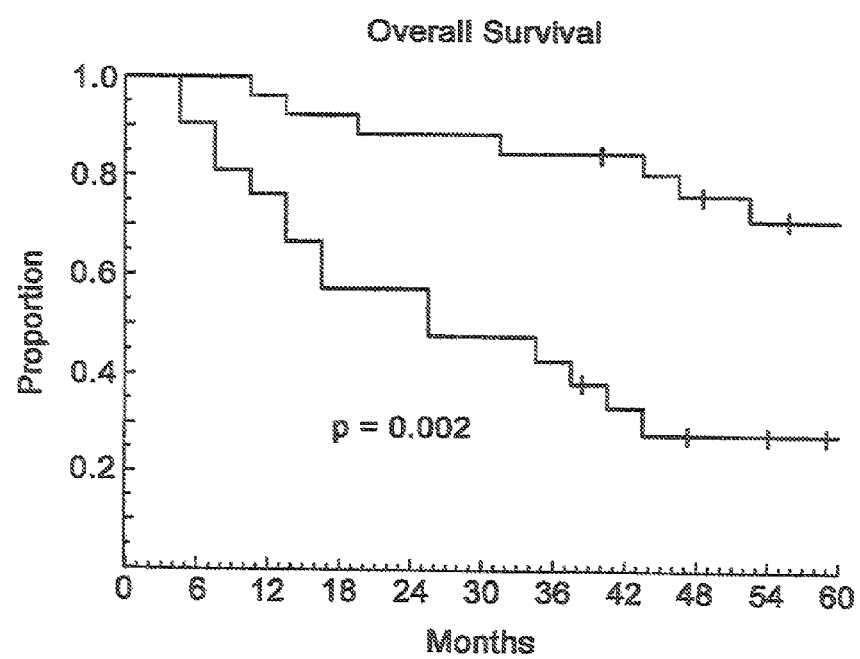

As shown in FIG. 3, a sample of pre-loaded DC showed that they expressed CD80 ($39.0 \pm 16.2\%$), CD83 ($7.1 \pm 6.9\%$), CD86 ($73.6 \pm 19.5\%$) and were MHC class II positive with a viability of $96.2 \pm 5.0\%$. The loaded DC had a significantly higher percentage of CD83 ($9.4 \pm 7.1\%$, p=0.019) with a significantly higher mean fluorescence intensity ($172.9 \pm 79.0$, p=0.0009) indicating that loading the DC with irradiated, IFN-gamma treated tumor cells induces maturation in some dendritic cells (FIG. 3B).

Discussion from First Study

Protocols for antigen loading, maturation, and administration, in the context of anti-tumor immunity, and guidance on dendritic cell (DC)-based immune therapy are practiced by the skilled artisan. This type of therapy encompasses use of purified autologous tumor cells as the source of antigen, and contains a patient-specific repertoire of tumor-associated antigens (Selvan (2010) Melanoma Res. 20:280-292; Dillman (2007) Cancer Biother. Radiopharm. 22:309-321). Some clinical trials are using unpurified autologous bulk tumors. This source of antigen may have contaminating fibroblasts and necrotic tissue (O'Rourke (2007) Melanoma Res. 17:316-322). Tumor stem cell associated antigens may be present in the purified cell lines (Dillman (2006) New Engl. J. Med. 355:1179-1181). IFN-gamma treatment increases expression of MHC class II molecules. MHC class II molecules are important for response to dendritic cell-based therapy. Molecules present in phagocytosed material, such as calreticulin, HMGB-1, and heat shock proteins, may contribute to a maturation signal, where this contribution may be in addition to contributions by cytokine cocktails. The present preparation of DCs shows a trend toward maturation, which can be associated with the phagocytosis of late stage apoptotic cells (Ip (2004) J. Immunol. 173:189-196). Use of apoptotic cells has been correlated with the generation of dendritic cells that were more effective at stimulating lymphocyte IFN-gamma secretion versus dendritic cells loaded with either tumor cell lysates or necrotic cells suggesting that dendritic cells loaded with apoptotic cells may be more potent in vivo. Resistance to the proapoptotic effects of IFN-gamma may be associated with a better clinical outcome (Comforth (2010) Cancer Immunol. Immunother. 60:123-131). Interleukin-12 (IL-12) secretion by mature DC can lead to robust cytotoxic lymphocyte (CTL; $CD8^+$ cells) activity. The issue of whether ex vivo maturation leads to lasting tumor immunity, has been addressed. The risk of induction of regulatory T cells, which can suppress antigen specific CTLs, by immature DC has also been shown to occur with cytokine matured DC. A re-evaluation of the sequence of signaling events that leads to maturation is being investigated to improve DC maturation protocols. Thus, the use of irradiated whole tumor cells as the antigen source in this study, without the necessity of ex vivo cytokine maturation, may be a more preferable method of DC immunotherapy since the evidence presented here indicates that the DC have begun the process of maturation. Upon injection, these "maturing" DCs may complete the process of maturation by secreting chemokines which will attract licensing, antigen-specific CD40L expressing $CD4^+$ T cells. Serum chemokines, like CCL17/TARC produced by dendritic cells in response to the adjuvant GM-CSF, have been associated with better progression-free survival rates. In some contexts, activation of lymphocytes by dendritic cells may require the expression of co-stimulatory molecules like CD80 and CD86. As a marker of maturation, CD83, is expressed on mature dendritic cells and may correspond to dendritic cells that can induce a more potent immune response (Prazma (2008) Immunol. Lett. 115:1-8). This represents a fraction of all the cells in the pharmaceutical preparation. The number of mature DCs alone, in any one pharmaceutical regiment, may or may not be correlated with a better patient response.

Table from the First Study

TABLE 1

Table I: Change in the expression level of common tumor associated antigens in response to interferon-gamma in melanoma cell lines used patient-specific cell based dendritic cell therapy.

| Antigens | No basal expression | Basal expression | Change after IFN-gamma treatment | |
|---|---|---|---|---|
| | | | None | Down |
| S-100 | 74.1% | 25.9% | 42.9% | 57.1% |
| HMB-45 | 18.5 | 81.5 | 54.5 | 45/5 |
| Mel-2 | 3.7 | 96.3 | 46.2 | 53.8 |
| Melan-A | 11.1 | 88.9 | 29.2 | 70.8 |
| Mel-5 | 18.5 | 81.5 | 72.7 | 27.3 |
| MAGE-1 | 51.9 | 48.1 | 38.5 | 61.5 |
| MART-1 | 11.1 | 88.9 | 14.8 | 85.2 |
| Tyrosinase | 25.9 | 74.1 | 40.0 | 60.0 |

N=27 samples.

Materials and Methods for the Second Study

Melanoma Cell Lines

The commercially available melanoma cell lines A375, SK-Mel-5 and SK-Mel-28 were purchased from American Type Culture Collection (Catalogue numbers: CRL-1619, HTB-70, and HTB-72). A375, SK-Mel-5, and SK-Mel-28 were maintained in 5% fetal bovine serum in RPMI-1640 (Invitrogen, catalogue number 11875-085). The pan-capase inhibitor, z-VAD-fmk and its control compound, z-FA-fmk, were purchased from BD Pharmingen (Catalogue numbers: 550377 and 550411). Transfections of GFP-LC3 were performed as per manufacturer instructions (InvivoGen, catalogue numbers psetz-gfplc3 and lyec-12) and photomicrograph were taken on an Olympus BX-51 microscope using a DP72 digital camera. Tumor cells lines were incubated with 1000 U/mL of IFN-γ (InterMune, Cat #) for 72 hours prior to assaying. Patient-specific cell lines were generated as described (Hamai (2008) Cancer Res. 68:9854-9864; Tyring (1984) J. Natl. Cancer Inst. 73:1067-1073) by enzymatic digestion of surgical tumor samples, cultivation in RPMI-1640 tissue culture media supplemented with fetal bovine and enriched calf serum (Omega Scientific, San Diego, Calif.) plus 1 mM sodium pyruvate, 1 mM glutamine and HEPES buffer. Phase contrast photomicrographs were taken on a Olympus CK-2 microscope using a Nikon DS-L1 digital microscope camera.

Autologous Dendritic Cell Generation

Dendritic cells were generated by plastic adherence method of ficoled apheresis products (Selvan (2007) Int. J. Cancer. 122:1374-1383; Cornforth (2010) Cancer Immunol. 60:123-131) in antibiotic-free AIM-V medium (Invitrogen, Cat#) supplemented with 1,000 IU/mL each of IL-4 (CellGenix, Cat#) and GM-CSF (Berlex, Seattle, Wash.) (DC medium). The flasks were then cultivated for 6 days prior to loading with IFN-gamma treated, irradiated autologous tumor cells.

Flow Cytometry

Analysis of tumor cell death and changes in major histocompatibility class II expression in response to IFN-gamma were conducted by use of antibodies directed against MHC class II, annexin-V and 7-amino-actinomycin D (7-AAD) and acquired on a Beckton-Dickenson FACS Calibur® flow cytometer.

Western Blotting

Melanoma tumor cell lysates were resolved on 10-12.5% SDS-PAGE, transferred to nitrocellulose and probed with primary antibodies overnight prior to secondary antibody conjugation and development by Novex AP Chromogenic substrate (Invitrogen, Carlsbad, Calif.) to develop bands. Antibodies against LC3-B antibodies (Cell Signaling Technologies, Boston, Mass.) and GADPH (EMD biosciences, Germany) were used at manufacturers recommended dilutions of 1:100 and 1:10,000, respectively.

Description of the Second Study

What was investigated was the induction of autophagy, apoptosis and MHC class II molecules after IFN-gamma treatment of melanoma tumor cells in vitro. Autologous and model melanoma tumor cell lines were incubated with 1000 IU/mL of IFN-gamma for 72 hours prior to assaying for autophagy, apoptosis and WIC class II expression. Autophagy was detected by immunoblotting with antibodies against LC3 II and by flow cytometry with Enzo's CytoID Autophagy Detection Kit. Apoptosis and MHC class II induction were assayed by flow cytometry using 7-AAD and annexin-V staining and antibodies against MHC class II, respectively.

Results of the Second Study

The results demonstrated that IFN-gamma induces both autophagic and apoptotic cell populations in melanoma cell lines. The apoptotic population is predominantly found in the non-adherent population while the autophagic cells remain adherent to the flask. Blocking of autophagy with the inhibitor 3-methyladenine (3-MA) inhibits the induction of MHC class II positive cells in response to IFN-gamma (39.4% IFN-gamma vs. 10.0% IFN-gamma+3-MA). Inhibition of caspase activity with the pan caspase inhibitor Z-VAD prevents apoptosis but does not perturb autophagy in IFN-gamma treated cells (2.75±0.15 IFN-gamma vs. 3.04±0.27 IFN-gamma+Z-VAD, fold change). Induction of apoptosis is associated with reduced levels of autophagy and WIC class II expression. Patients receiving autologous tumor cell loaded dendritic cells that are non-apoptotic autophagic cells derived from interferon-gamma treated purified tumor cell lines have improved progression-free and overall survival (p 0.003 and p 0.002, respectively). A procedure to eliminate apoptotic cells while retaining viable autophagic cells after IFN-gamma treatment may enhance the effectiveness of this type of cell-based immunotherapy.

Pooled Analysis of Studies

Autologous, proliferating, self-renewing tumor cells (putative tumor stem cells and/or early progenitor cells), are important to establishment of new depots of metastatic cancer, and may be excellent sources of antigen for vaccines. These studies addressed the impact on survival from immunizing with antigens from such cells.

Methods

Data was pooled from three successive phase II trials, all of which included patients with documented metastatic melanoma, who were treated in protocols that utilized antigens from cell cultures of autologous tumor cells. S.C. injections were given weekly for 3 weeks, then monthly for 5 months: 74 patients were injected with irradiated tumor cells (TC): 54 patients were injected with autologous dendritic cells (DC) that had been co-cultured with irradiated autologous tumor cells (NCI-V01-1646): in a randomized phase II trial, 24 patients were injected with TC, and 18 with DC.

Results

Table 2 summarizes overall survival (OS) in each trial. In the pooled analysis there were 98 TC and 72 DC patients. Characteristics were similar in terms of age (51, 52), male gender (62%, 62%), no evidence of disease at the time of treatment (46%, 47%), and presence of MU visceral disease at the time of treatment (13%, 14%). OS was longer in patients treated with DC (median 63.1 vs 20.2 months, 5-year OS 51% vs 26%, p=0.0002 Mantle-Cox log-rank test). The difference in OS in the randomized trial is also significant (p=0.007).

Patient-specific DC vaccines primed with antigens from autologous proliferating, self-renewing tumor cells are associated with encouraging long-term survival rates, and are superior to patient-specific TC vaccines in populations of patients who have been diagnosed with metastatic melanoma.

TABLE 2

| Vaccine | # patients | # deaths | Median OS | 2-yr OS | 5-yr OS |
|---|---|---|---|---|---|
| TC | 74 | 60 | 20.3 mos | 45% | 28% |
| DC (Use IFN-gamma treated melanoma cells) | 54 | 31 | 58.4 mos | 72% | 50% |
| TC | 24 | 16 | 15.9 mos | 31% | — |
| DC (No IFN-gamma treatment of melanoma cells) | 18 | 5 | Not Reached | 72% | — |

The survival curves from the three trials of patient specific vaccines are shown in FIG. 13. Consecutive phase I and II clinical trials were conducted using autologous tumor cells, in combination with autologous dendritic cells or without the dendritic cells, were conducted. Subcutaneous injections were given weekly for three (3) weeks, then monthly for five (5) months, 74 patients were injected with irradiated tumor cells without pretreatment with IFN-gamma (TC): 54 patients were injected with autologous dendritic cells (DC) that had been co-cultured with irradiated autologous tumor cells with pretreatment with IFN-gamma: in a randomized phase II trial, 24 patients were injected with TC without pretreatment without IFN-gamma, and 18 with DC plus TC without pretreatment with IFN-gamma.

FIG. 14 shows survival curves from three trials, where the trials are the same clinical trials as those disclosed in FIG. 13, but with additional data acquired from later time points, as is evident from comparing the step plots in the two figures. The melanoma cells in the clinical trials, TC-24 and TC-74, did not receive IFN-gamma. The melanoma cells in the clinical trial, DC-TC-18, did not receive IFN-gamma. The melanoma cells in the clinical trial, DC-TC-54, did get IFN-gamma.

A non-limiting standard operating procedure for preparing dendritic cell vaccine includes the following (Table 3). Upon harvesting tumor cells after expansion, the following are to be made for each patient's tumor cell lot. What is needed is about 220 million cells to make the tumor cell vaccine lot. Any extra cells are to be cryopreserved as back up cells. Make stock cell suspension as $220 \times 10^6$ cells in 22 ml medium to distribute in the following manner (Table 3).

TABLE 3

| Use | Total cell # needed | First action | Second action | Final disposition |
|---|---|---|---|---|
| TC Vaccine Doses or DC Loading Cells | 150 million | 15 ml from the stock to a 50 ml conical tube, add 25 ml AIM-V, and irradiate | Cryopreserve cells after irradiation in 10 small cryovials. | Store until needed for patient treatment. |

Trial #2: DC 2000-2006 (NCI-V01-1646). Phase II Trial of Autologous Dendritic Cells Loaded with Antigens from Irradiated Autologous Tumor Cells as Patient Specific Vaccines (BB-IND 8554): Dendritic Cell (DC) Vaccine. In the production of the vaccine for this trial, autologous proliferating tumor cells were co-incubated with IFN-gamma, cryopreserved, and then subsequently co-incubated with autologous dendritic cells. Each aliquot of cells was suspended in 500 micrograms of GM-CSF for injection Trial #3: DC vs. TC 2007-2011 (NCT00436930): Randomized Phase II Trial Of Autologous Vaccines Consisting Of Adjuvant GM-CSF plus Proliferating Tumor Cells Versus GM-CSF Plus Dendritic Cells Loaded With Proliferating Tumor Cells In Patients With Metastatic Melanoma (BB-IND 8554 and BB-IND 5838): 'MAC VAC.' The third trial was a randomized trial to determine whether there was a difference in the two approaches noted above. IFN-gamma was not used in the production of the tumor cells. As in the DC trial above, all patients were randomized to receive either TC or DC injected s.c. with 500 micrograms of GM-CSF, weekly for 3 weeks and then monthly for five months. The projected 72% 2-year survival rate for patients in the DC arm is comparable to the 71% observed 2-year survival observed in the previous 54-patient trial of DC in which the median survival was five years.

Thus, while there have shown and described and pointed out fundamental novel features of the disclosure as applied to an exemplary implementation and/or aspects thereof, it will be understood that various omissions, reconfigurations and substitutions and changes in the form and details of the exemplary implementations, disclosure and aspects thereof may be made by those skilled in the art without departing from the spirit of the disclosure and/or claims. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or implementation may be incorporated in any other disclosed or described or suggested form or implementation as a general matter of design choice. It is the intention, therefore, to not limit the scope of the disclosure. All such modifications are intended to be within the scope of the claims appended hereto.

All publications, patents, patent applications, references, and sequence listings, cited in this specification are herein incorporated by this reference as if fully set forth herein.

The Abstract is provided to comply with 37 CFR §1.72(b) to allow the reader to quickly ascertain the nature and gist of the technical disclosure. The Abstract is submitted with the understanding that it will not be used to interpret or limit the scope or meaning of the claims.

What is claimed is:

1. A melanoma vaccine comprising:
    a population of melanoma cells comprising melanoma peptides from a subject with melanoma, contacted, in vitro, with an antigen presenting cell (APC) from the same subject,
    wherein the population of melanoma cells
    (a) is selected for being at least 60% autophagic, non-apoptotic, and MHC class II expressing, by one or more of flow cytometry, affinity chromatography, immunomagnetic separation, or adherence to a tissue culture surface;
    (b) is not treated with IFN-gamma;
    (c) is metabolically active;
    (d) is treated, in vitro, with an inhibitor of apoptosis, and
    wherein the contact between the melanoma cells and the APCs results in APCs comprising the melanoma peptides that are partially or substantially processed.

2. The composition of claim 1, wherein the APC is a dendritic cell.

3. The composition of claim 1, wherein the population of melanoma cells comprise melanoma-specific peptides that are acquired by the APCs and are partially or substantially processed in the APCs.

4. The composition of claim 1, wherein the APCs are loaded with melanoma specific peptides derived from the population of melanoma cells.

* * * * *